US012806404B2

(12) United States Patent
Ayre et al.

(10) Patent No.: US 12,806,404 B2
(45) **Date of Patent: *Nov. 24, 2026**

(54) IMPLANTABLE DEVICE AND DELIVERY METHOD

(71) Applicant: Northern Research AS, Oslo (NO)

(72) Inventors: Peter Ayre, Frenchs Forest (AU); John Begg, Fitzroy Falls (AU); Tor Kristoffersen, Oslo (NO)

(73) Assignee: Northern Research AS, Oslo (NO)

( * ) Notice: Subject to any disclaimer, the term of this patent is extended or adjusted under 35 U.S.C. 154(b) by 273 days.

This patent is subject to a terminal disclaimer.

(21) Appl. No.: 18/630,081

(22) Filed: Apr. 9, 2024

(65) Prior Publication Data

US 2024/0252811 A1 Aug. 1, 2024

Related U.S. Application Data

(63) Continuation-in-part of application No. 17/052,047, filed as application No. PCT/AU2019/050399 on May 2, 2019, now Pat. No. 11,980,750.

(30) Foreign Application Priority Data

May 3, 2018 (AU) ................................ 2018901493

(51) Int. Cl.
*A61M 60/139* (2021.01)
*A61M 60/165* (2021.01)
(Continued)

(52) U.S. Cl.
CPC ........ *A61M 60/515* (2021.01); *A61M 60/165* (2021.01); *A61M 60/232* (2021.01);
(Continued)

(58) Field of Classification Search
CPC .............. A61M 60/139; A61M 60/135; A61M 60/232; A61M 60/515; A61M 60/531;
(Continued)

(56) References Cited

U.S. PATENT DOCUMENTS

2002/0019577 A1* 2/2002 Arabia ................ A61M 60/531 600/16
2008/0097226 A1* 4/2008 McConnell .......... A61B 5/0215 600/16

(Continued)

*Primary Examiner* — Eugene T Wu
(74) *Attorney, Agent, or Firm* — Benesch Friedlander Coplan & Aronoff LLP

(57) ABSTRACT

An implantable device, adapted for assisting the flow of blood from left atrium to an aorta of an in-vivo heart, includes an inlet cannula and an outlet cannula in fluid communication with an implanted blood pressure pump. A first accelerometer is mounted on a housing of the blood pressure pump and is adapted for measuring mitral valve motion. An external controller is in electrical communication with at least one implanted ECG sensor adapted for detecting ECG signals. The at least one implanted ECG sensor is positioned between the implanted blood pressure pump and the external controller. The external controller includes a processor adapted to analyse detected ECG signals and the mitral valve motion. The processor dynamically adjusts a target blood pressure pump speed based on ECG signals and the mitral valve motion such that blood flows from left atrium to left ventricle and then to the aorta.

9 Claims, 11 Drawing Sheets

(51) Int. Cl.

| | |
|---|---|
| ***A61M 60/232*** | (2021.01) |
| ***A61M 60/515*** | (2021.01) |
| ***A61M 60/585*** | (2021.01) |
| ***A61M 60/90*** | (2021.01) |

(52) U.S. Cl.
CPC .......... *A61M 60/585* (2021.01); *A61M 60/90* (2021.01); *A61M 2205/04* (2013.01); *A61M 2205/103* (2013.01); *A61M 2205/3303* (2013.01); *A61M 2205/3327* (2013.01); *A61M 2205/3365* (2013.01); *A61M 2205/502* (2013.01); *A61M 2210/125* (2013.01); *A61M 2210/127* (2013.01); *A61M 2230/04* (2013.01); *A61M 2230/62* (2013.01); *A61M 2230/63* (2013.01)

(58) Field of Classification Search
CPC .............. A61M 60/569; A61M 60/592; A61M 60/816; A61M 60/861; A61M 60/896; A61M 2205/15; A61M 2205/18; A61M 2205/3334; A61M 2205/3507; A61M 2205/3553; A61M 2205/8206; A61M 2230/04; A61M 2230/62; A61M 2230/63; A61M 60/165; A61M 60/865; A61M 60/855; A61M 60/113; A61M 60/148; A61B 17/00; A61B 17/3468; A61B 17/3423; A61B 2017/00243; A61B 2017/3425; A61F 2/2436; A61F 2/2472; A61F 2/2412; A61F 2250/0002; A61F 2250/0013; A61F 2/243; A61F 2/2418; A61F 2/2466; A61F 2/82; A61F 2/482; A61F 2/848; A61F 2/89; A61F 2/95; A61F 2002/8486
See application file for complete search history.

(56) References Cited

U.S. PATENT DOCUMENTS

| | | | | |
|---|---|---|---|---|
| 2008/0183287 | A1* | 7/2008 | Ayre .................. | A61M 60/585<br>623/3.28 |
| 2010/0179611 | A1* | 7/2010 | O'Brien ............. | A61N 1/36514<br>607/17 |
| 2019/0160214 | A1* | 5/2019 | Garrigue ............. | A61M 60/148 |

* cited by examiner

IMPLANTABLE DEVICE AND DELIVERY METHOD

CROSS-REFERENCED TO RELATED APPLICATIONS

This application is a continuation-in-part application and claims priority and the benefit of U.S. patent application Ser. No. 17/052,047 filed on Oct. 30, 2020, which is a National Stage Entry of PCT/AU2019/050399 filed on May 2, 2019, which claims priority to Australian Patent Application No. 2018901493. These applications are incorporated herein by reference in their entirety.

TECHNICAL FIELD

The present disclosure may relate to an implantable device and delivery method. More particularly, the device of the present disclosure may be an implantable valve device and delivery device and delivery method. The present disclosure may also relate to system and method of controlling a blood pump to assist the functioning of a heart. More particularly, the system and method relate to optimally operating a centrifugal implanted blood pump from left atrium to aorta, of which various physiological parameters of the patient are considered for determining the optimal blood pump speed.

BACKGROUND

Conventional approaches for implantation of cardiac devices require the cutting of a relatively large opening in a patient's sternum or thoracic cavity in order to allow a surgeon to access a patient's heart. Commonly, these procedures require arrest of the patient's heart and a cardiopulmonary bypass which is the use of a heart-lung bypass machine to oxygenate and circulate the patient's blood). These procedures are generally followed by a prolonged hospitalisation and recovery time for the patient. Further, tissue adherences resulting from the first surgery may increase the risks associated with recovery, such as stroke and death, associated with subsequent valve replacement surgeries.

Synthetic valves and biological valves have been used for cardiac valve replacement. Synthetic valves do not often fail but require life-long anti-coagulant treatment to prevent blood from clotting in and around the replacement valve. Such anti-coagulant treatment significantly limits patients' activities and can cause various other complications. Biological valves do not require such anti-coagulation treatment but typically fail within 10-15 years. To limit the need for and risks associated with re-operation on failed biological valves, patients with relatively smaller life expectancies are provided with biological valve replacements, and patients with longer life expectancies have received synthetic valves and a continuing anti-coagulant treatment regime.

In view of the above risks, there have been a number of attempts made to develop less-invasive surgical methods for cardiac valve replacement. These surgical methods, referred to as percutaneous heart valve replacement therapies (PHVT), use a catheter to deliver a replacement valve to an implantation site using the patient's vascular system. These PHVT attempts have various shortcomings, including their inability to ensure proper positioning and stability of the replacement valve within the patient's body.

Other known devices typically require difficult implant procedures and may be incredibly time sensitive as they may require a temporary artificial pumping assistance for a patient's heart. It is common practice to induce a cardiac arrest to stop the heart to allow for implantation of a medical device for the heart. During this procedure the patient will be kept alive via external devices. This can cause a number of complications for the patient and also increases the recovery time for the patient.

Therefore, it may be advantageous to provide for a device which may reduce the risk involved with conducting cardiac surgery, and associated treatments therefor. Further, it may be advantageous to reduce the need for such invasive procedures to implant a cardiac device, such as a valve or delivery port.

Other cardiac pumping devices for pumping blood from the left atrial to descending thoracic aorta is described in U.S. Pat. No. 4,143,425 for example. However, there is no consideration about optimal pumping speeds requiring the mitral valve to be openable while the pumping device is in use. The inability to ensure pump speeds such that mitral valve can open during a cardiac cycle may lead to blood clots from lack of blood flow from the left atrium to the left ventricle and/or left atrium. This may also cause a number of life threatening complications for the patient including cardiac embolism, pulmonary embolism and stroke.

Any discussion of the prior art throughout the specification should in no way be considered as an admission that such prior art is widely known or forms part of common general knowledge in the field.

SUMMARY

In one embodiment, an implantable device is adapted for assisting the flow of blood from left atrium to an aorta of an in-vivo heart. The implantable device includes an inlet cannula adapted to be connected to the left atrium and an outlet cannula adapted to be connected to the aorta, wherein the inlet and outlet cannula is in fluid communication with an implanted blood pressure pump.

The implantable device includes a first accelerometer mounted on the housing of the blood pressure pump, wherein the first accelerometer is adapted for measuring mitral valve motion.

The implantable device includes an external controller in electrical communication with at least one implanted ECG sensor adapted for detecting ECG signals, wherein the at least one implanted ECG sensor is positioned between the implanted blood pressure pump and the external controller; and wherein the external controller comprises a processor adapted to analyse detected ECG signals, and the mitral valve motion; and wherein the processor dynamically adjusts a target blood pressure pump speed based on ECG signals and mitral valve motion such that blood flows from left atrium to left ventricle and then to the aorta.

DETAILED DESCRIPTION

Problems to be Solved

Figure 1:
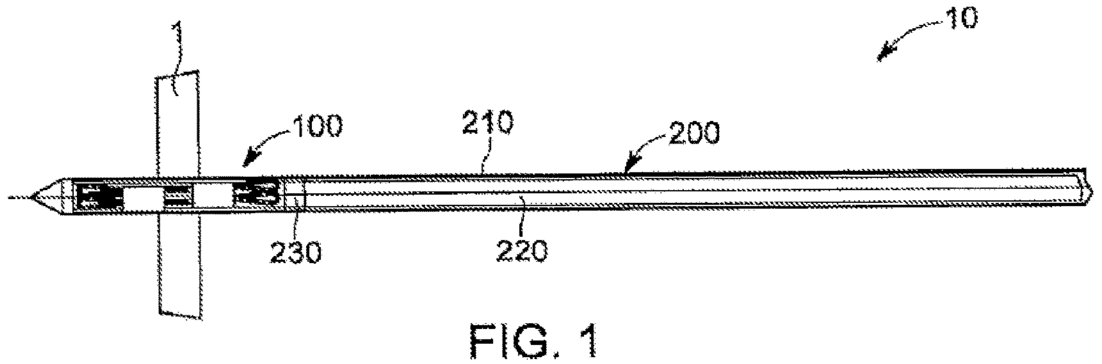
FIG. 1 illustrates an embodiment of a first stage of deployment of an implantable device via a delivery device.

It may be advantageous to provide for a device which does not require cardiac arrest to be installed.

It may be advantageous to provide for a device which can be implanted via keyhole surgery.

It may be advantageous to provide for a delivery device which does not require open heart surgery.

It may be advantageous to provide for a valve which can be implantable in a patient via a delivery device.

It may be advantageous to provide for a device which prevents fluid loss when in use.

It may be advantageous to provide for a device which conforms to the shape of surrounding site tissue to encourage growth of tissue.

It may be advantageous to provide for an implantable device for measuring and determining patient posture and patient activity.

It may be advantageous to provide for an implantable device that can operate the blood pump speed such that blood can be pumped from the left atrium to the aorta while allowing the mitral valve to open during the cardiac cycle to allow for blood to flow from the left atrium to the left ventricle to discourage blood clotting in the heart.

It may be advantageous to provide for an implantable device that can set safe blood pump speeds depending on the patient's activity and posture.

It may be advantageous to provide for an implantable device that has a processor to analyse, calculate and operate the blood pump optimally with changing patient posture and activity over time.

It may be advantageous to provide for an implantable device that can selectively fluctuate target speed between maximised target speed and minimum target speed to replicate the cardiac cycle.

It may be advantageous to provide for an implantable device with external controllers so as to minimise implantable parts in the body, which can be easily maintained external to the body.

It is an object of the present invention to overcome or ameliorate at least one of the disadvantages of the prior art, or to provide a useful alternative.

Means for Solving the Problem

In a first aspect there may be provided an implantable device being deliverable by a delivery device, the implantable device comprising a body portion having a lumen extending in an axial direction from a proximal end to a distal end; a first abutment means disposed on the body portion near to the distal end; the abutment means being deployable from a compacted position to an expanded position; and wherein a valve is disposed in the lumen of the body portion such that the valve deploys to a sealing configuration when the body portion is in an expanded position.

Preferably, a second abutment means disposed on the body portion. Preferably, the second abutment means is expandable. Preferably, at least one of the first abutment means and the second abutment means is adapted to expand before the body portion can expand. Preferably, the first abutment means is bias towards the second abutment means when each of the first abutment means and second abutment means is expanded. Preferably, body portion is self-expandable. Preferably, the proximal body portion is flared. Preferably, the first abutment means comprises at least one rib. Preferably, the body portion comprises an internal structure comprising a shape memory material. Preferably, the valve comprises a plurality of leaflets. Preferably, the body portion is a stent.

In a further aspect, there may be provided a method for delivering an implantable device to a target site; the method comprising the following steps: making an incision in target site tissue; advancing a delivery device through the incision in the target site tissue; displacing a sheath of the delivery device relative to an implantable device within the sheath proximal of a first abutment means such that the first abutment means expands to form an abutting relationship with a first side of the target site tissue; further displacing the sheath proximal of a second abutment means such that the second abutment means expands and forms an abutting relationship with an second side of the target site tissue; and expanding a stent connected to the first abutment means and the second abutment means and withdrawing the delivery device.

Preferably, the method further comprises suturing at least one of the first abutment means, the second abutment means and the stent to the target site tissue. Preferably, the first side of the target site tissue and the second side of the target site tissue are opposing sides. Preferably, a valve is deployed in the stent when the delivery device is withdrawn. Preferably, a medicament delivery device is implanted in the stent. Preferably, the medicament delivery device is sutured to the stent.

In a further aspect, there may be provided an implantable device adapted for assisting the flow of blood from left atrium to descending aorta of an in-vivo heart, the implantable device comprising: an inlet cannula adapted to be connected to the left atrium and an outlet cannula adapted to be connected to the descending aorta, wherein the inlet and outlet cannula is in fluid communication with a blood pressure pump; a first accelerometer mounted on the housing of the blood pressure pump, wherein the first accelerometer is adapted for measuring mitral valve motion; an implanted controller in electrical communication with at least one implanted ECG sensor adapted for detecting ECG signals, wherein the at least one implanted ECG sensor may be positioned between the blood pressure pump and the implanted controller; the implanted controller may comprise a processor adapted to analyse detected ECG signals, and the mitral valve motion; the processor dynamically adjusts the target blood pressure pump speed based on ECG signals and mitral valve motion such that the blood flows from the left atrium to both the left ventricle and the descending aorta.

Preferably, the first accelerometer may be adapted to measure a first shift of coordinate data based on the movement of the first accelerometer.

Preferably, the implanted controller may comprise a second accelerometer, wherein the second accelerometer may be mounted on the implanted controller.

Preferably, the second accelerometer may be adapted to measure a second shift of coordinate data based on the movement of the second accelerometer.

Preferably, the first shift of coordinate data, and the second shift of coordinate data may be analysed by the processor for detecting patient postures and patient activities, wherein each patient activity may have a predetermined blood pressure pumping speed.

Preferably, the processor may be adapted to calculate an optimal blood pressure pumping speed based on the patient posture and patient activity.

Preferably, when the optimal blood pressure pumping speed may be within the predetermined blood pressure pumping speed for the determined patient activity, the processor may dynamically operate the blood pressure pump with the optimal blood pressure pumping speed.

Preferably, when the optimal blood pressure pumping speed may be outside of the predetermined blood pressure pumping speed for the determined patient activity, the processor may dynamically operate the blood pressure pump with the predetermined blood pressure pumping speed.

Preferably, the implantable device may further comprise an electrical lead, wherein a first end of the electrical lead may be connected to the implanted controller, and a second end of the electrical lead may be connected to an external controller.

Preferably, the external controller may comprise a battery, wherein the battery may be housed in the external controller.

Preferably, the external controller may be in electrical communication with an external monitor and a power source, wherein the external monitor may be adapted to display at least one of the group of: aortic pressure data, atrial pressure data, ventricular pressure data, ventricular volume data, electrocardiogram data, phonocardiogram data, blood pressure pump flow data, blood pressure pump speed data, blood pressure pump power data, and mitral valve motion data.

In a further aspect, there may be provided an implanted controller adapted for driving a centrifugal implanted blood pump, wherein the pump may be connected between left atrium to aorta and is driven at predetermined target speed by the controller; the controller may detect mitral valve motion and may amend target speed to maximise target speed wherein the mitral valve motion is periodic during cardiac cycle and wherein the target speed is above a calculated minimum target speed; and wherein the controller may detect posture and activity of user of the pump and calculates the minimum target speed.

Preferably, the controller may classify posture and activity as one of three predetermined states.

Preferably, the controller may selectively fluctuate target speed between maximised target speed and minimum target speed to replicate cardiac cycle.

In a further aspect, there may be provided an implantable device adapted for assisting the flow of blood from left atrium to an aorta of an in-vivo heart, the implantable device comprising: an inlet cannula adapted to be connected to the left atrium and an outlet cannula adapted to be connected to the aorta, wherein the inlet and outlet cannula is in fluid communication with an implanted blood pressure pump; a first accelerometer mounted on the housing of the blood pressure pump, wherein the first accelerometer is adapted for measuring mitral valve motion; an external controller in electrical communication with at least one implanted ECG sensor adapted for detecting ECG signals, wherein the at least one implanted ECG sensor is positioned between the implanted blood pressure pump and the external controller; and wherein the external controller comprises a processor adapted to analyse detected ECG signals, and the mitral valve motion; and wherein the processor dynamically adjusts a target blood pressure pump speed based on ECG signals and mitral valve motion such that blood flows from left atrium to left ventricle and then to the aorta.

Preferably, the first accelerometer is adapted to measure a first shift of coordinate data based on the movement of the first accelerometer.

Preferably, further comprising an electrical lead in electrical communication between the implanted blood pressure pump and the ECG sensor, wherein a second accelerometer is disposed in the electrical lead.

Preferably, the second accelerometer is adapted to measure a second shift of coordinate data based on the movement of the second accelerometer.

Preferably, the first shift of coordinate data, and the second shift of coordinate data are analysed by the processor for detecting patient postures and patient activities, wherein each patient activity has a predetermined blood pressure pumping speed.

Preferably, the processor is adapted to calculate an optimal blood pressure pumping speed based on the patient posture and patient activity.

Preferably, when the optimal blood pressure pumping speed is within the predetermined blood pressure pumping speed for the determined patient activity, the processor dynamically operates the blood pressure pump with the optimal blood pressure pumping speed. Or preferably, when the optimal blood pressure pumping speed is within the predetermined blood pressure pumping speed for the determined patient activity, the processor dynamically operates the blood pressure pump with the optimal blood pressure pumping speed.

Preferably, the implantable device may further comprise a second electrical lead, wherein a first end of the second electrical lead is connected to the ECG sensor, and a second end of the second electrical lead is connected to the external controller.

Preferably, the second electrical lead has a textured silicone surface.

In the context of the present invention, the words "comprise", "comprising" and the like are to be construed in their inclusive, as opposed to their exclusive, sense, that is in the sense of "including, but not limited to".

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention.

Preferred embodiments of the invention will now be described with reference to the accompanying drawings and non-limiting examples.

The following reference numbers appear in the illustrated embodiments:

1—organ wall
2—aorta
3—direction of flow
10—device
20—medicament delivery device
100—implantable device/valve
100A—implantable device variant for aorta
101—stent/body portion
102—stent lumen
105—bridging structure
110—proximal concertina
120—distal concertina
130—outer wall
132—inner wall
140—valve
150—inner abutment means
151—inner membrane
152—inner membrane periphery
160—ribs
160A—long ribs
160B—short ribs
162—distal end of rib
164—tapered portion
166—proximal end of rib
170—outer abutment means
171—outer membrane
172—outer membrane periphery
180—ribs
182—distal end of rib
184—tapered portion
186—proximal end of rib
190—suture/attachment means
200—delivery device
202—head
204—cutting means
210—sheath
211—distal end of sheath
215—lumen
216—aperture
220—inner element
230—pusher An embodiment of a device 10 including a delivery device 200 and an implantable device 100 are shown in FIGS. 1 to 4. In the illustrated embodiment, the implantable device 100 is a valve device 100. The valve device 100 is being installed in a wall of the heart 1 of a patient. Suitable locations for the device 100 to be mounted, may include the aortic valve, aorta, atrium, mitral valve, pulmonary cardiac valve, ventricle or other desired location of the heart. Preferably, the valve device 100 is implantable in the wall of a left atrium of a patient heart. However, it will be appreciated that the device 100 may be implanted in other organs or target tissue.

The delivery device 200 may be a catheter or other similar device which can be used in keyhole surgery or other minimally invasive surgery. The delivery device 200 has a distal end and a proximal end with the head 202 of the device being at the distal end. The proximal end of the delivery device 200 is preferably external the patient and at a handle (not shown) operated by a clinician.

The head 202 at the distal end is preferably of a diameter which is substantially the same as the diameter of the sheath 210. The head 202 is preferably in contact with the sheath 210 before insertion into a patient such that the implantable device 100 is contained in the sterile environment inside the lumen 215 of the sheath 100. The lumen 215 of the sheath 210 may extend from the proximal end to the distal end of the sheath 210, with the distal end of the sheath having an aperture 216 through which the implantable device 100 can be ejected or deployed. A pusher 230 or plunger may be used to push the implantable device 100 in an axial direction relative to the sheath 210. Alternatively, the pushed 230 may be locked in a fixed position and the sheath 210 can be withdrawn while the inner element 220 and the pusher 230 remain stationary relative to the withdrawing sheath 210, and therefore the head 202 and the implantable device 100 also remain stationary relative to the withdrawal of a sheath 210. The axial direction is in the longitudinal axis of the lumen 215, and the implantable device 100 is displaceable relative to the sheath 210. More preferably, the implantable device 100 and the sheath 210 are movable relative to each other, such that the implantable device can be positioned distal of the sheath 210. The pusher 230 is preferably in contact with the inner wall of the sheath 210 defining the lumen 215 such that a seal is formed between the pusher 230 and the inner wall of the sheath 210. The seal may prevent or restrict the ingress of fluids, such as blood, into the delivery device 200. Head 202 may form a seal with the sheath 210. The seal between the head and the sheath 210 may be a frangible seal which is broken with the relative movement of the head 202 to the sheath 210.

An inner element 220 may be used to move the pusher 230 to push or project the implantable device 100 distal of the sheath 210. As can be seen, the head 202 is also projected distal of the sheath to allow for the implantable device to deploy between the sheath 210 and the head 202. The sheath 210 may be formed from any desired biocompatible material. Optionally, the sheath 210 may be formed from a relatively rigid material to reduce adverse compression or movement of the implantable device 100 while in the lumen 215 of the sheath 210.

Figure 4:
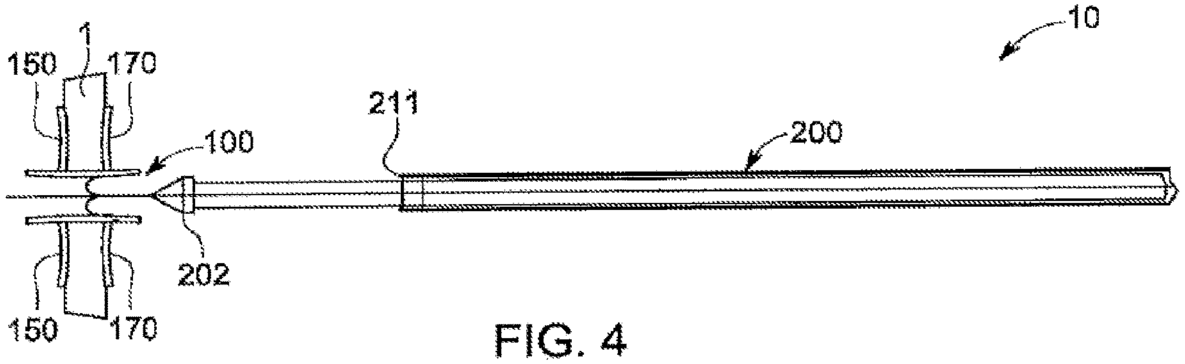
FIG. 4 illustrates an embodiment of a further stage of deployment of an implantable device via a delivery device in which the device is deployed.

A cutting means 204 is disposed on head 202 which can be used to make an incision in an organ 1 or through tissue. The cutting means 204 may be any desired means to make an incision or aperture within an organ 1 or tissue. The cutting means may be a blade, or a plurality of blades in any predetermined arrangement. For example the blades may form a cross, a star, a straight edge, a linear shape, a circle, an eyelet, or any other regular or desired shape to form an aperture suitable for the head 202 to penetrate tissue. The tissue incision may be smaller than the diameter of the head 202, such that the head 202 is to be urged into the incision for a tight fit of the implantable device 100. Alternatively, the incision can be at least as big as the diameter of the head 202 such that the head 202 is easily insertable, and the implantable device 100 abuts the aperture formed by the incision, as seen in FIG. 4. In yet another embodiment, the head 202 is a penetrating tip, or a non-cutting head, or is adapted to pass through an incision which is pre-cut or preformed before insertion of the device. In this embodiment, the head 202 does not have a cutting means.

The implantable device 100 is mountable proximal the distal end 202 of the delivery device 200 and is housed within the lumen 215 of sheath 210 of said delivery device 200. The lumen 215 may be of a uniform diameter or cross sectional area, such that the inner element 220 is free to move within the length of the lumen 215. Optionally, the inner element 220 conforms to the shape of the lumen 215, such that variances in the cross section of the lumen 215 may restrict the movement of the inner element 220. The inner element 220 may be relatively more rigid than the sheath 210, such that the inner element may push the implantable device 100 within the lumen 215 or be used to impart a shape to the sheath 210. At the distal end of the inner element 220 is a pusher 230 which can be used to push or abut the implantable device 100.

The implantable device 100 may be anchored to the organ 1 by an abutment means and/or a suture. The abutment means 150, 170 may press against the walls such that the implantable device 100 is fixed in a desired position. It is preferred that tissue will be allowed to grow over inner abutment means 150 and/or outer abutment means 170. At least one of the abutment means 150, 170 may be stitched, sutured or sewn to the tissue being abutted, or may be stitched, sutured or sewn to the other abutment means through the organ wall 1. If the inner abutment means 150 is to be stitched, sutured or sewn to the organ 1, but the outer wall is not to be stitched, sutured or sewn, the implantable device 100 may be partially deployed such that the outer abutment means 170 remain within the sheath while the inner abutment means 150 are stitched, sutured or sewn to the organ 1.

Figure 5:
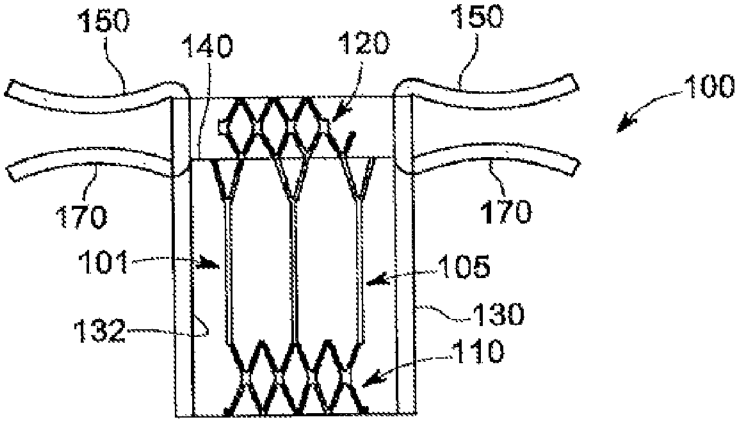
FIG. 5 illustrates a side view of embodiment of an implantable valve.

The abutment means 150 may be formed with a membrane (inner membrane 152), which is spread out or stretched into a desired configuration or shape by ribs 160. The ribs have a focal point which is the longitudinal axis of the wall of the implantable device 100. The longitudinal axis is parallel to the elements of the bridging structure 105, as seen in FIG. 5, or more generally the longitudinal axis is parallel to the walls 130, 132 extends in the direction of the lumen 215. Bound between the outer wall 130 and inner wall 132 is a support structure which is shown as bridging structure 105. The support structure includes a proximal structure 110, a distal structure 120 and a bridging structure 105 which links the two structures 110, 120 together. The proximal structure 110 illustrated in FIG. 5 is a concertina type structure, similarly distal structure 120 is also a concertina type structure.

The implantable device 100 may have a valve 140 used to allow for insertion of a further device, such as a medicament delivery device 20, such as a cannula or needle. The valve 140 may block fluid passing through the valve 140 unless desired. For example, the implantable device 100 has a valve 140 disposed near to the abutment means 150, 170. As shown in FIG. 5, the valve 140 is positioned proximal the plane of the outer abutment means 170. The valve 140 may comprise at least one leaflet, or a plurality of leaflets, or a tricuspid type valve, which can form a seal to prevent, or substantially prevent fluids passing through the valve. The valve leaflets may be flexible to allow for the leaflets to move for an extended period of time without damage. Further, the leaflets may be formed from an elastic material and be biased in a predetermined position. The leaflets of the valve 140 may be integrally formed with the wall inner wall 132 of the stent 101 of the implantable device 100, or the valve 140 may be mounted in the stent lumen of the implantable device 100. The stent lumen 102 is defined by inner wall 132. Optionally, the valve 140 may be removably mounted in the lumen of the implantable device 100.

The valve 140 may be an "artificial valve" which may be a biological or synthetic valve introduced into the patient's body through surgery. A synthetic valve may optionally be a mechanical valve. The implantation site for an implantable device 100 (or other replacement valve) typically includes at least a part of the area with a failed valve and/or along at least a portion of adjacent structure(s), such as a wall of an organ. The implantable device 100 may include a biological material (e.g., tanned, untanned, heterologous or autologous), non-biological material, a synthetic material, or a combination thereof. In some embodiments, valve 140 may include preserved biological tissue such as, for example, human tissue (e.g., homografts, autografts of valve tissue) or animal tissue (heterograft or xenograft valve tissue). In some embodiments, valve 140 may be a mechanical valve.

When valve 140 is a biological valve, expansion of implantable device 100 from a collapsed configuration to an expanded may require self-expansion of stent 101, and therefore the body of the implantable device 100 may be capable of self-expansion. Implantable device 100 may have a shape/form (e.g., length, width, diameter, etc.) corresponding to that of the intended application, at least when the implantable device is deployed and/or expanded. The number of flaps or leaflets of the valve 140 may correspond to the use of the device 100 and/or the organ being implanted. The valve 140 may have at least one leaflet, but preferably comprises a plurality of leaflets. In other embodiments, valve 140 may have any other suitable number of flaps and/or other physical characteristics (e.g., diameter, length, width, etc.).

The stent 101 includes at least one of; the outer wall 130, the inner wall, the bridging structure 105, the proximal structure 110 and the distal structure 120. Preferably, the stent 101 includes each of the outer wall 130, the inner wall, the bridging structure 105, the proximal structure 110 and the distal structure 120. Each component of the stent 101 may be disposed between the outer and inner walls 130 and 132. The ribs 160, 180 of each of the inner and outer abutment means 150, 170 may also be part of the stent 101.

Collectively, the bridging structure 105, the proximal structure 110 and the distal structure 120 may be referred to as a "stent" 101. In at least one embodiment, the stent 101 preferably includes outer wall 130 and inner wall 132. Optionally, the stent may also include the ribs 160, 180 of the abutment means 150, 170. The ribs of the abutment means are preferably housed or embedded within the membrane of the abutment means. The ribs 160 of the inner abutment means 150 are preferably embedded in the membrane 151 such that they do not move relative to the membrane 151. Similarly, the outer abutment means 170 may be formed with the ribs 180 embedded in the membrane 171. Each membrane 151, 171 has a respective periphery 152, 172.

Figure 6:
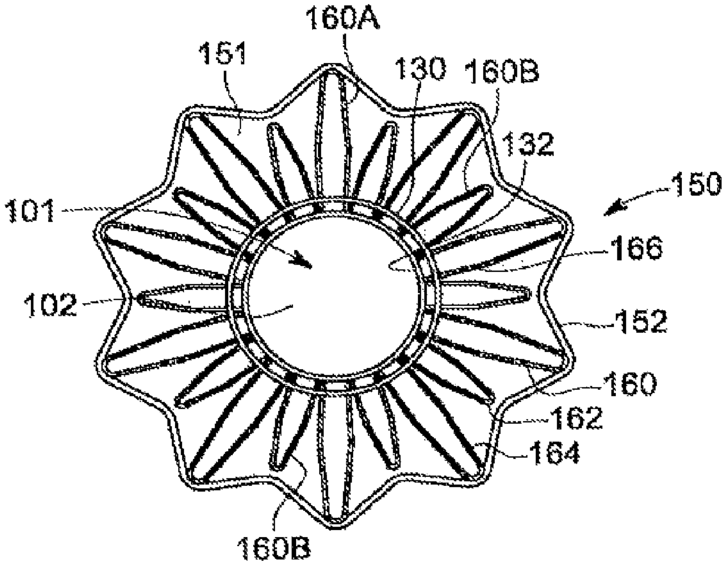
FIG. 6 illustrates a top view of an embodiment of an inner abutment means of the valve.

Ribs 160, 180 may be arranged in any predefined arrangement, however it is preferred that at least one rib 160, 180 extends from the stent 101 towards the periphery 152, 172 of the respective membrane 151, 171. The ribs 160, 180 may be considered to be arranged radially of the longitudinal axis of the stent 101. Each rib 160, 180 may be comprised of a pair of arms which are formed from a single element, such as a wire or other elongate element. The ribs 160, 180 are preferably formed from a shape memory alloy, shape memory material or the like. The ribs 160 of the inner abutment means 150 are shown as an array of large ribs 160A and small ribs 160B, with the membrane periphery being proximal, or attached to, the distal ends 182 of each of the ribs 160A, 160B. In this way the ribs 160 cause the periphery 152 of the membrane 151 to form a star shape or burst shape as seen in FIG. 6. Other configurations may also be formed irrespective of the rib shape and/or length. Preferably, the periphery of the membrane 151 spans from the distal end of a first rib to a second rib. The second rib may or may not be directly adjacent to the first rib. Optionally, only one distal end of a rib is proximal the periphery of the membrane.

Figure 7:
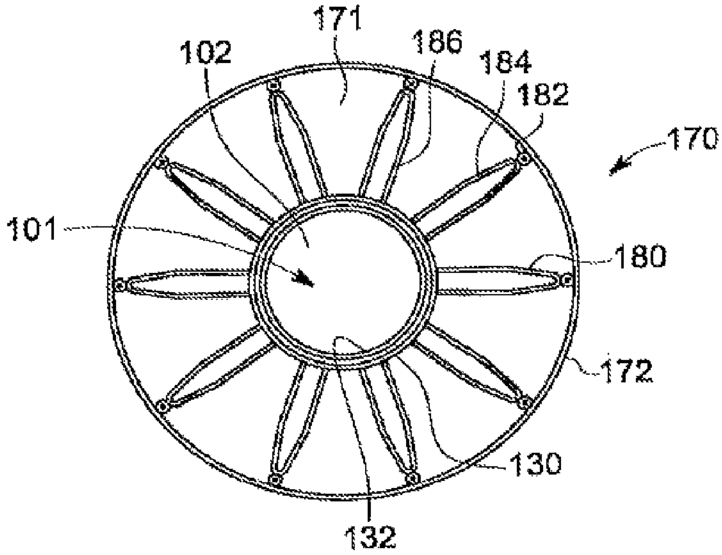
FIG. 7 illustrates a bottom view of an embodiment of an outer abutment means of the valve.

In an unillustrated embodiment, the periphery 152, 172 of the abutment means 150, 170 may be shaped by a shape memory alloy or the membrane 151, 171 may be formed into a predetermined shape. Optionally, the periphery of the membranes may be relatively thicker than the portion of the membrane covering the length of the ribs, as seen in FIGS. 6 and 7. Having the periphery of a relatively thicker material may allow for the ribs to remain in the membrane without puncturing the periphery, which may be of particular concern when being deployed.

Implantable components may be formed from polymers, synthetic organic material, biocompatible organic material, ceramics and biocompatible metals. Metals may include at least one of; titanium, nitinol, gold, platinum, stainless steel, cobalt-chromium alloys, and other commonly used biocompatible alloys. Further, the delivery device 200 may be formed from similar biocompatible materials. For example, the sheath 210 of the delivery device 200 may be formed from PEBAX®, polymer, or have polymer coating such that the sheath 210 material does not react with any tissue or fluids when in use.

In another embodiment, implantable device 100 can be mounted in the aorta 2 of the patient. The implantable device 100, 100A may be deployed in a similar manner as that of previous embodiments described herein. The abutment means of the device 100A are shaped such that the abutment is specific to the tissue implantation site contours. This may assist with forming a sufficient seal between the device 100A and the tissue. Having a shaped or contoured abutment means may allow for reduced damage to surrounding tissue and may encourage tissue growth over the membrane, and therefore improving the potential for recovery without infection or rejection of the device 100, 100A.

FIG. 1 illustrates an embodiment of an implantable device 100 fully encapsulated within the lumen 215 of the delivery device 200. The head 202 of the delivery device 200 has penetrated the wall of an organ 1. In this embodiment, the organ wall 1 is a left atrium of a patient heart. The cutting means 204 on the head 202 is used to make an incision or cut into the organ 1, which forms an aperture, and the head 202 of the delivery device 200 is pushed therethrough. The proximal portion of the head 202 of the delivery device 200 is in contact with the distal end of the sheath 210 and a fluid tight seal may be formed therebetween, such that fluids cannot ingress the lumen 215 of the delivery device 200, at least before deployment of the implantable device 100.

Figure 2:
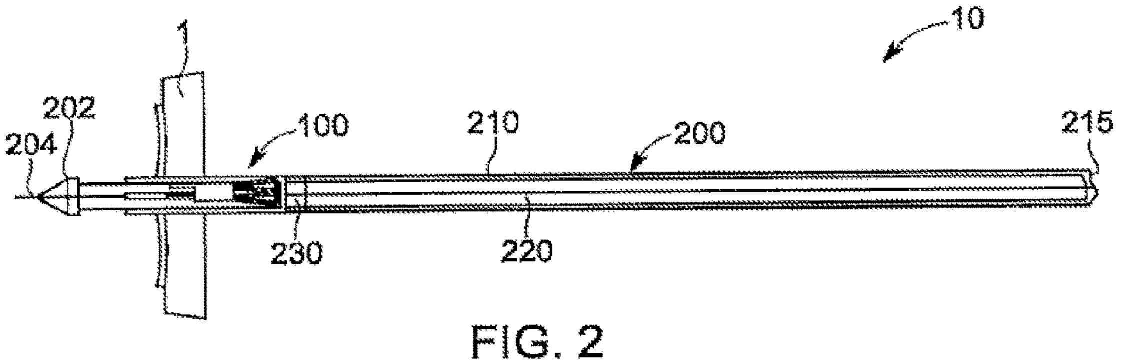
FIG. 2 illustrates an embodiment of a further stage of deployment of an implantable device via a delivery device.

To break the seal between the head 202 and the sheath 210, the clinician may push the inner element 220 forward to break the seal, or withdraw a portion of the sheath, while the head 202 remains stationary. FIG. 2 illustrates the relative movement of the sheath 210 to the head 202. As the head 202 is projected distal the distal end 211 of the sheath 210 the first abutment means 150 will no longer be confined by the sheath 210 and the shape memory alloy, or other shape memory material of the first abutment means will cause the first abutment means to deploy. The first abutment means 150 may be inner abutment means 150. The shape memory alloy or shape memory material may be the ribs 160. Optionally, the membrane 151 material may also comprise or be formed from a shape memory material.

Once the implantable device 100 is in a position ready to be deployed, the sheath 210 can be retracted, or the inner element advanced, and the inner abutment means 150 of the device 100 can be deployed. If the abutment means 150 is deployed in a position in which the abutment means 150 is not in contact with the inner tissue wall, or does not fully deploy, the clinician can move the delivery device 200 (with implantable device 100 therein) axially until the abutment means has deployed correctly. After this time the sheath 210 can be further retracted such that the outer abutment means 170 can be deployed against the outer tissue wall. It will be appreciated that the abutment means 150, 170 are biased towards each other, such that the tissue between the abutment means 150, 170 is compressed, gripped or otherwise pinched between the pair of abutment means 150, 170. Once both abutment means 150, 170 are in a desired abutting position, the stent 101 can be opened. The opening (expansion) of the stent 101 may occur once both abutment means are deployed, or may occur when the head 202 of the delivery device 200 is withdrawn. If the stent 101 is deployed when the head 202 is withdrawn, the stent 101 may comprise a frangible component that can break with the removal of the head to cause the expansion of the stent 101.

If the stent 101 has a valve 140 installed, the valve 140 also deploys when the head moves passed the valve 140 in the direction of the outer abutment means 170, or in other words when head 202 moves proximal the valve 140. In this way, the device 100 can be installed and there is little or negligible fluid loss when implanting the device 100. Further, using this method and device, the organ or tissue being implanted can remain active during the procedure. This is a significant advantage as recovery times can be drastically reduced, operation times may be reduced, and overall costs for the patient and clinician can be reduced.

Figure 3:
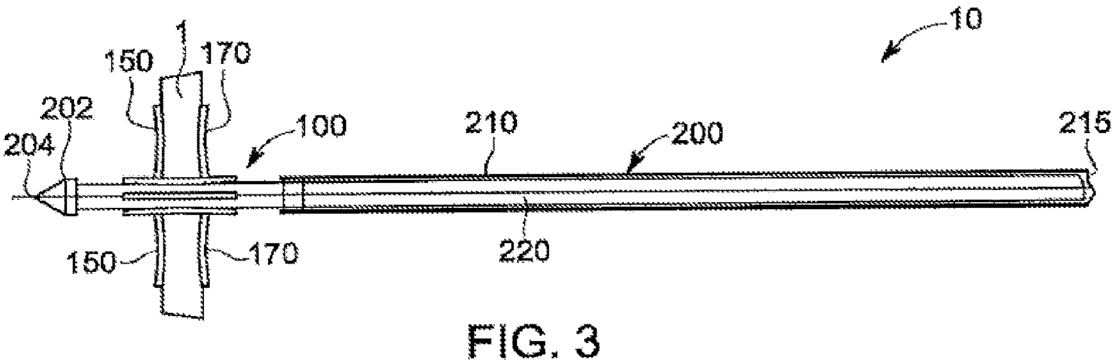
FIG. 3 illustrates an embodiment of a yet a further stage of deployment of an implantable device via a delivery device.

FIG. 3 illustrates a further relative displacement between the head 202 and the sheath 210. The sheath 210 may be moved by the clinician such that the second abutment means 170 can be released from the sheath 210. The second abutment means 170 may be the outer abutment means 170. The shape memory alloy or shape memory material may be the ribs 180. Compression of both of the first and the second abutment means 150, 170 against the organ wall may be sufficient to retain the implantable device 100 in the desired position, but not damage tissue or cause tissue being abutted to lose blood flow. The abutment means may also compress tissue to allow for clotting at the periphery of the abutment means membrane, but not allow for regions of stagnant blood to form. In this way, the device 100 may assist patient recovery, and reduce the potential for infection, stroke or a pulmonary embolism.

While the valve 140 is illustrated as being located adjacent the outer abutment means 170, the valve may be located in any desired position to reduce the volume of the stent 101 which may house blood or other fluids when the valve 140 is sealing a portion of the stent 101, to reduce the potential for stagnant blood, or adverse clotting. For example, the valve 140 may be positioned near to the inner abutment means 150, however any desired position in the stent lumen 102 may be used. However, if the leaflet(s) of the valve 140 are positioned in the stent 101 closer to the outer abutment means 170, the length of the valve leaflet(s) may be less than, or equal to, the distance of the valve seal location and the distal end of the stent 101. It may be advantageous to limit the length of the leaflets such that they do not exceed the distal end of the stent 101 such that they do not interfere with flow of fluid when a cannula or stylet 20 is inserted into the stent 101.

Referring to FIGS. 2, there is shown the inner abutment means deployed against the inner wall of an organ 1. When the sheath 210 is displaced proximal of the inner abutment means 150, the inner abutment means 150 may expand or otherwise open to the deployed position. The expansion may be automatic once the inner abutment means is free from the sheath 210. The expansion may be caused by a shape memory material, such as the shape material of the ribs 160 of the membrane 151.

Referring to FIG. 3, the sheath 210 has been moved further proximally the outer abutment means which causes the outer abutment means to deploy. The outer abutment means may deploy automatically, similar to that of the inner abutment means. However, it will be appreciated that after the inner abutment means 150 and the outer abutment means 170 the stent 101 can also be deployed or expanded. The outer wall 130 and inner wall 132 of the stent of the implantable device 100 are shown as being compressed as the stent 101 is in an unexpanded position. The expansion of the stent 101, can be automatic when the sheath 210 is removed from around the implantable device 100. Alternatively, the expansion of the stent 210 may occur when the head 202 of the delivery device 200 is withdrawn trough the stent 101. In yet another embodiment, at least one of the sheath 210, the inner element 220 or the pusher 230 may have an activation means which causes the expansion of the stent 101 when displaced proximally of the implantable device 100.

The stent 101 may be biased to be in a compressed position or unexpanded position when the sheath 210 is around the implantable device 100. Further, the stent 101 may also be in the compressed position or unexpanded position when the sheath 210 has been removed and the head 202 of the delivery device 200 is distal the distal end of the stent 101. In either case, the does not allow the flow of fluid therethrough during deployment of the implantable device 100.

The valve 140 may be a plurality of leaflets such that the leaflets may form an iris seal or form any other desired seal. The iris may be advantageous as the stent may be expanded to any desired size and the valve 14 may still form an appropriate seal to prevent blood or other fluids from passing through the stent 101 undesirably. In another embodiment, the leaflets are curved and substantially press against the inner wall 132 of the stent 101 when a medicament delivery device 20 is inserted. In this way, haemostasis can be enhanced or improved by the device 100. Optionally, the medicament delivery device 20 may be fixed to the device 100 when in use. At least one of the stent 101, or abutment means 150, 170, may be provided with at least one suture location which allows for suturing the medicament delivery device 20 to the device 100 in a desired location such that the medicament delivery device 20 does not move undesirably.

FIG. 4 illustrates the removal of the delivery device 200 and the expansion of the stent 101 and the valve 140 forming a seal across the stent 101. Removal of the stent 101 may be prevented by the abutment means 150, 170. Further, removing the head 202 through the stent 101 may cause the stent to deploy or expand. The expansion of the stent is preferably limited by the size of the incision. It will be appreciated that the size of the incision may be smaller than the maximum size of the stent 101 such that an adequate seal may be formed. However, if the incision is larger than desired, a further stent (not shown) may be deployed within the incision to reduce the size of the aperture (incision) such that the implantable device 100 may be installed. Alternatively, an incision relatively than the fully expanded stent 101 will allow for a full expansion the stent 101, and abutment means 150, 170 are used to prevent or substantially prevent fluid loss, or fluid passing through the aperture formed by the incision.

Optionally, the outward radial forces of the stent 101 may be sufficient enough to fully expand to a predetermined diameter or cross sectional area, regardless of the size of the incision. In this way, the cross sectional area/diameter of the valve may be known or anticipated, such that a stylet, cannula or other medicament delivery device 20 may be inserted without damaging the valve 140 or stent 101 of the implantable device 100.

The outer portion proximal end of the stent 101 may be flared or tapered (see FIG. 4) to assist with insertion of a stylet 20 or cannula 20. It is preferred that the cross sectional shape of the stent is a circle or ovoid as this may provide a generally even outward force to compress against the incision. It will be appreciated that as an incision is typically longitudinal, the stent 101 may have regions which may exert a larger outward force, or radial force, in the regions relative to the direction of the incision such that undesired pressure is not exerted on a portion of the incision.

A sectional side view of an implantable device 100 is shown in FIG. 5. The implantable device comprises a pair of abutment means 150, 170 which are biased towards each other. A stent 101 is shown with a shape memory skeleton formed from proximal concertina 110, distal concertina 120 and bridging structure 105. Each concertina 110, 120 may be attached to a respective end of the bridging structure 105. Alternatively, a shape memory skeleton of a uniform structure may be provided for a stent 101. The stent 101 may be expandable or self-expandable. The ribs 160, 180 of each respective abutment means 150, 170 is illustrated in FIGS. 6 and 7. Optionally, in an unillustrated embodiment, the proximal portion of the stent 101 and/or the proximal concertina 110, has a skirt or other flared structure to assist with placement of a medicament delivery device 20 into the lumen of the stent 101. The single expandable structure may be a uniform structure, such as a single concertina type structure, or other expandable structure. In yet another embodiment, the internal structure is a liquid structure, which is separated into two chemical components, such that when the head 202 of the delivery device 200 is withdrawn, the two chemical components mix and cause the desired expansion to abut the aperture of the head 202.

An embodiment a top view of the inner abutment means 150 is illustrated in FIG. 6. The ribs 160 radially extend from the stent 101 and comprise a pair of arms, with the pair of arms portion proximal the stent 101 being relatively parallel 166, and the distal end 162 of the arms near to the stent 101 being tapered 164 towards each other and meeting near the periphery 152. The periphery 152 of the membrane 151 as shown may be a star or burst shape, but may also be any other desired shape such as a circle, or other polygon. The periphery 152 of the membrane 151 may optionally be reinforced or otherwise thicker to reduce the potential for breaks or punctures. The ribs 160 may extend from the stent 101 and be integrally formed therewith, or fixed therewith. Each rib 160 as illustrated may be spaced from an adjacent rib 160, whereas the ribs 160 of the inner abutment means may be abutting adjacent ribs as is shown proximal the stent lumen 102.

The periphery of the membrane 152 may be defined by the rib array. The rib array comprises two sets of ribs 160A, 160B. The ribs are alternating in 1-2-1 arrangement such that a short rib is positioned between two long ribs 160. Each of the long ribs 160A and short ribs 160B may have a pair of arms with the portion proximal the stent 101 being relatively parallel, and the portion proximal the periphery 152 having the arms taper towards each other 162 at the end distal the stent 101. Alternatively, each of the long ribs 160A and/or the short ribs 160B may be formed with a single arm extending from the stent to the periphery.

FIG. 7 shows an embodiment of a view of the outer abutment means 170. Similar to FIG. 6, the ribs 180 comprise a pair of arms, with the pair of arms portion proximal the stent 101 being relatively parallel 186, and the distal end 182 of the arms near to the stent 101 being tapered 184 towards each other and meeting proximal a spacer 182. At the distal end of the arms is a ring, pledge or spacer 182, which is positioned between the arms 180 and the periphery of the membrane 171. The spacer 182 can receive a suture to fix the membrane 171 to the tissue. The periphery 172 of the membrane 171 as shown may be generally circular, but may also be any other desired shape. The periphery 172 of the membrane 171 may optionally be reinforced or otherwise thicker to reduce the potential for breaks or punctures. The ribs 180 may extend from the stent 101 and be integrally formed therewith, or fixed therewith. Each rib 180 as illustrated may be spaced from an adjacent rib 180, whereas the ribs 160 of the inner abutment means may be abutting adjacent ribs as shown in FIG. 6.

It will be appreciated that any desired rib 160, 180 shape may be used with the present invention. Each rib 160, 180 may be separately connected to the stent 101, or alternatively a plurality of the ribs 160, 180 may be connected to a collar (not shown) which is connected to the stent 101. In this way the device 100 may be adapted to have swappable components before implantation. Swappable components may include inner abutment means 150, outer abutment means 170, calve 140 and/or stent 140.

When the inner abutment means and the outer abutment means are fixed or otherwise attached to the stent 101, the elongate ribs 160 of the inner abutment means 150 may be positioned such that they are disposed between the ribs 180 of the outer abutment means 170. The shorter ribs 160B may be aligned with, or substantially aligned with the ribs 180 of the outer abutment means 170. It will be appreciated that the inner and outer abutment means configurations may be swapped. In yet another embodiment, the inner 150 and outer 170 abutment means may have the same rib array, or rib structure. It will be appreciated that in this way, the tissue 1 between the inner abutment means 150 and the outer abutment 170 is compressed in a way to reduce the potential for leaks to form, or tissue to have restricted blood flow causing stagnant blood or clots.

The membranes 151, 171 may be formed from the same material as the inner and outer walls 132, 130. It will be appreciated that the thickness of the walls may be substantially the same as, or thicker, than the membranes 151, 171 of the outer and/or inner abutment means. The periphery 152, 172 of the membrane 151, 171 maybe reinforced, or may be thicker to reduce the potential for puncturing from the ribs or degradation from fluid flow. In yet another embodiment, the inner wall 132 is formed from a different material than the outer wall 130, as outer wall 130 may wish to encourage tissue growth while the inner wall may be desired to abut the medicament delivery device 20.

Figure 8:
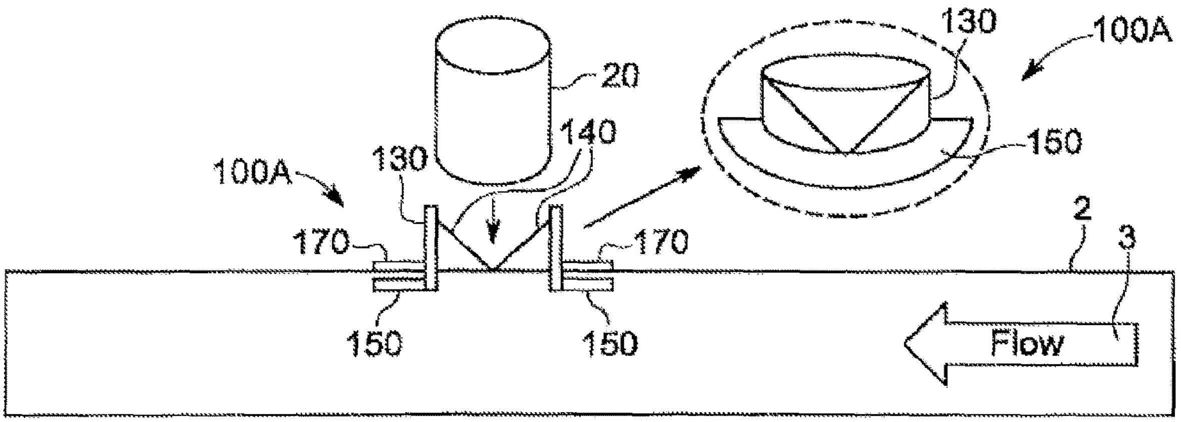
FIG. 8 illustrates yet another embodiment of a valve deployed in an aorta of a patient.
Figure 9:
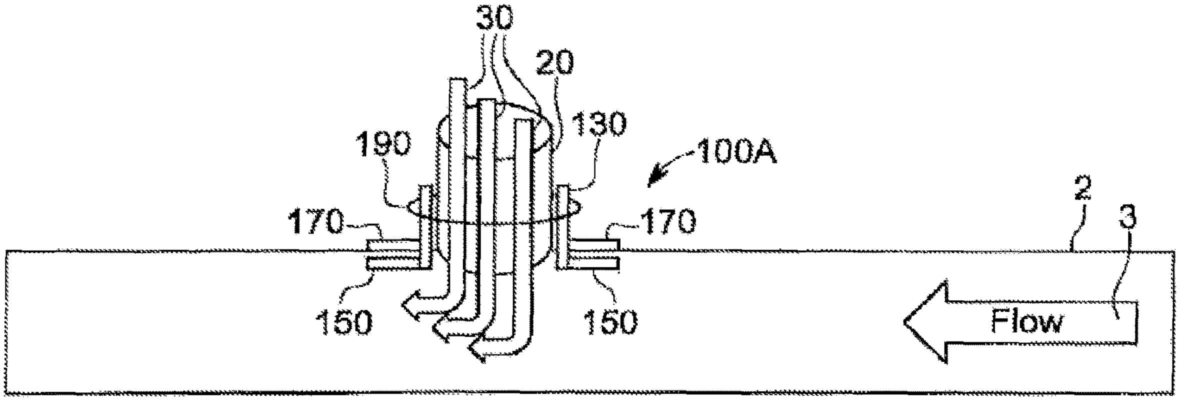
FIG. 9 illustrates yet another embodiment of a valve deployed in an aorta of a patient with a cannula for delivery of a medicament.

FIGS. 8 and 9 illustrate an embodiment of an implantable device 100A mounted on the aorta of a patient. Surrounded by a dashed circle is a side view of an embodiment 100A. The abutment means 150, 170 of the implantable device 100 are shown as rounded such that they conform to the natural shape of the aorta 2 or the natural shape of the organ 1 to be mounted on. It will be appreciated that the abutment means 150, 170 may be any predetermined shape to be mounted to a desired organ. Preferably, the abutment means have shape memory material which conforms the respective abutment means membranes to the desired shape. The stent 101 comprises a valve 140 through which a cannula or other medicament delivery device 20 can be inserted, as shown in FIG. 9. The stent 101 comprises a pair of abutment means 150, 170. The inner abutment means 150 is in contact with a flow of fluid when installed, such as the flow of blood 3 through the aorta 2. The direction of flow may also dictate the shape of the inner abutment means 150 such that the periphery being first in contact with the direction of flow 3 is relatively thinner to allow for an advantageous hydrodynamic flow of fluid across the inner abutment means 150. Other shapes and configurations may also be used which improve the flow of fluids across the surface of the device and reduce undesirable coagulation or clotting. The side of the abutment means 150, 170 in contact with tissue may have a texture or other grip improvement means to reduce movement of the device 100 relative to the tissue implantation site.

Within the dashed circle of FIG. 8 there is illustrated a device 100A which is mounted to an aorta of a patient. The device 100A is similar to the device of FIG. 5, however the inner and the outer abutment means are shaped to conform to the rounded shape of the tissue at the implantation site. The curved shape of the abutment means 150, 170 may be similar to each other to be mounted to a linear thickness wall.

As can be seen in FIG. 9, after insertion of a medicament delivery device 20, fluids may be delivered into the organ 1 or target site. The delivery of fluids may also increase or decrease the pressure near to the implantation site to result in a more desirable flow. Optionally, sensors may be placed on the medicament delivery device 20, in the stent 101 or on the abutment means to detect at least one of; internal pressures, fluid pressures, fluid loss, fluid flow rate, volume of fluid or any other desired sensing. The medicament delivery device 20 may also be removed after use, and the valve 140 will return to a biased position, which is preferably a closed position.

The pressure between the inner 150 and the outer 170 abutment means is such that the tissue compressed between the two abutment means may still receive blood and therefore oxygen, which will reduce the potential for dead tissue to form. Textures may also be provided on the abutment means, and at least a portion of the stent 101 to encourage tissue growth thereon. It is preferred that once the device 100 is installed, the device 100 is to remain implanted until the patient organ expires or the patient expires.

Valve 140 may be secured to the stent 101 via any suitable securing mechanism or combination of securing mechanisms. For example, in one embodiment, valve 140 may be sutured with one or more stitches to stent 101. In another embodiment, valve 140 may be secured to stent 101 by way of a friction fitting. For example, valve 140 may have a fully-expanded diameter that is slightly larger than the expanded diameter of stent 101 such that components 140 and 101 fit securely together upon expansion of valve 140 within stent 101.

The stent 101 may include microscopic hooks and valve 101 may include corresponding microscopic loops (or vice-versa). This hook-and-loop fastening system may include a micro-velour material, which has been used previously for surgical applications to improve tissue in-growth. Such a hook-and-loop fastening system may allow the position of valve 140 to be fine-tuned relative to the position of stent 101, for example, after components 140 and 101 have been implanted within a patient's body. The hooks/loops may also facilitate blood clotting and the formation of a seal at the interface between valve 140 and stent 101. To avoid premature clot formation (e.g., excessive clot formation before installation is complete), anti-coagulation monitoring and/or treatment may be provided to the patient. Reliable hook-and-loop connections may still be achieved in the presence of premature clot formation, although higher activation pressure (described below) may be required. A preliminary evaluation shows that reliable hook-and-loop connections can be formed in the presence of water, jelly, liquid soap, and/or coagulating proteins.

In some embodiments, stent 101 may have a diameter slightly larger than a diameter of the implantation site such that delivery and expansion of stent 101 at the implantation site secures stent 101 in place by way of a friction fitting. In some embodiments, stent component 101 may include one or more projections (e.g., spikes) or clasps for anchoring stent 101 to the failed valve and/or adjacent structure(s) at the implantation site.

In at least one embodiment, the inner abutment means 150 is positioned to be in the flow path of a fluid circulation system, and the outer abutment 170 means is positioned away from the circulatory system. In yet another embodiment, the inner and outer abutment means may both be in direct fluid flow, such as the fluid flow of a circulatory system.

In yet another embodiment, it will be appreciated that only a single abutment means may be provided, which can be deployed and sutured to the target location for use. In this way the device materials can be reduced, while allowing for the device 100 to be installed at a target tissue site.

It will be appreciated that at least one of the stent 101, the inner abutment means 150 and the outer abutment means 170 are deployable from a compressed position, contracted position or compacted position to an expanded position or deployed position. When the implantable device 100 is within the lumen 215 of the delivery device 200, the implantable device is in a compressed position, contracted position or compacted position, and outside of the lumen can be in an expanded position, open or deployed position. Simply, the implantable device may be in an undeployed position, a semi-deployed position, and a deployed position. The undeployed position being in the delivery device 200, the semi-deployed position when is when at least a portion of the device is within the lumen 215 of the delivery device 200 and/or the head 202 has not been withdrawn from the stent 101, and a deployed position when the delivery device 200 is withdrawn and/or when the implantable device is in a desired position and the stent is expanded.

The ratio of the inner abutment means 150 to the outer abutment means 170 may be in the range of 0.5:1 to 1:0.5. Further, the ratio of the stent 101 to at least one abutment means is in the range of 2:1 to 1:2. In an unillustrated embodiment, the abutment means 150, 170 may have at least one spur or hook which may mount in tissue when the abutment means 150, 170 are deployed.

Optionally, the abutment means 150, 170 may have preattached sutures, or a pulling means, which can be used to retract the abutment means 150, 170 after deployment. This may be advantageous if the implantable device 100 needs to be moved or removed. A catheter or the delivery device 200 may be adapted to pull the preattached sutures (or pulling means) to allow for retraction of the abutment means 150, 170 to the undeployed position or a semi-deployed position, and at least be partially contracted into the lumen 215.

Optionally, the stent 101 and/or the delivery device 200 may have preattached sutures 190. The stent lumen 102 may comprise at least one suture 190 such that a medicament delivery device 20, or a pump component can be inserted into the stent lumen 102 and attached to the sutures. The attachment method may be, for example, a parachute technique method (not shown), which is common in the art, but is used to reduce the overall procedure time. The parachute suture technique may be employed prior to the insertion of the implantable device 100 or partially performed, such that after implantation of the implantable device 100, the parachute technique can be completed and the sutures drawn closed to complete the suturing of the pump/medicament delivery device 20 to the stent 101. It will be appreciated that any desired suture technique may be used.

In another embodiment of present invention, the implantable device may have control algorithms for detecting the cardiac needs of the patient by inferring a range of physiological parameters. The control algorithm may be basic algorithm and/or an improved or smart algorithm. The physiological parameters may be at least one of selected from the group of: encephalogram (ECG), mitral valve activity, heart motions, patient posture and physical activity, heart rate, and respiration.

Figure 10A:
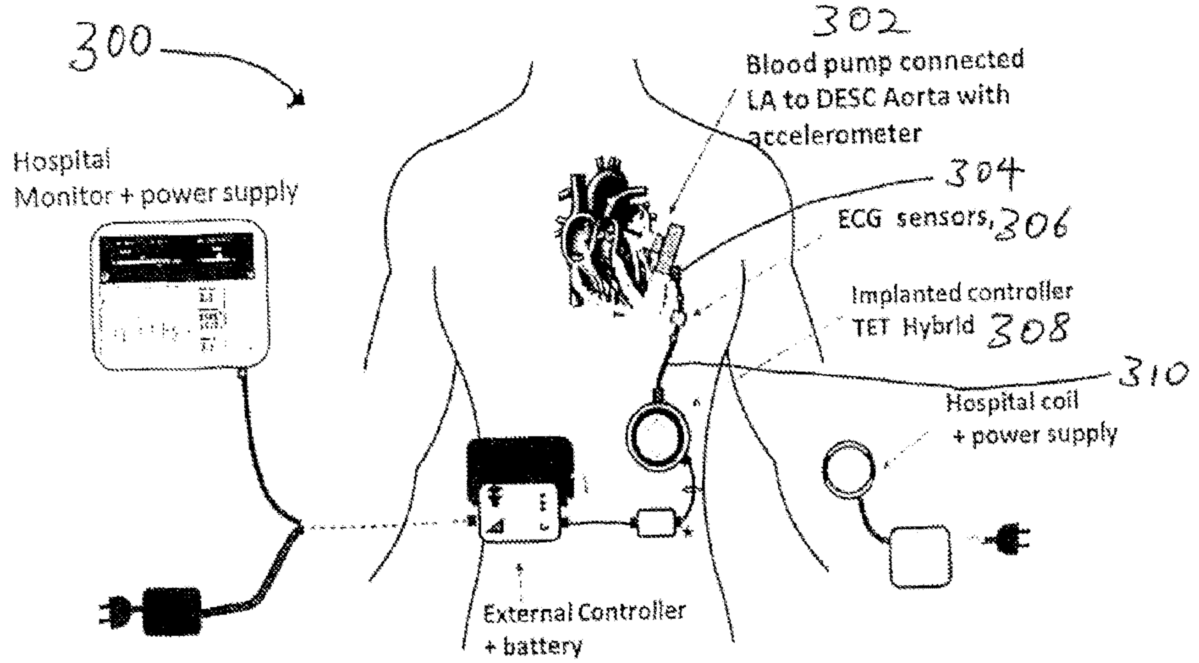
FIG. 10A illustrates a further embodiment of an implantable device adapted for assisting the flow of blood from left atrium to descending aorta of an in-vivo heart.
Figure 10B:
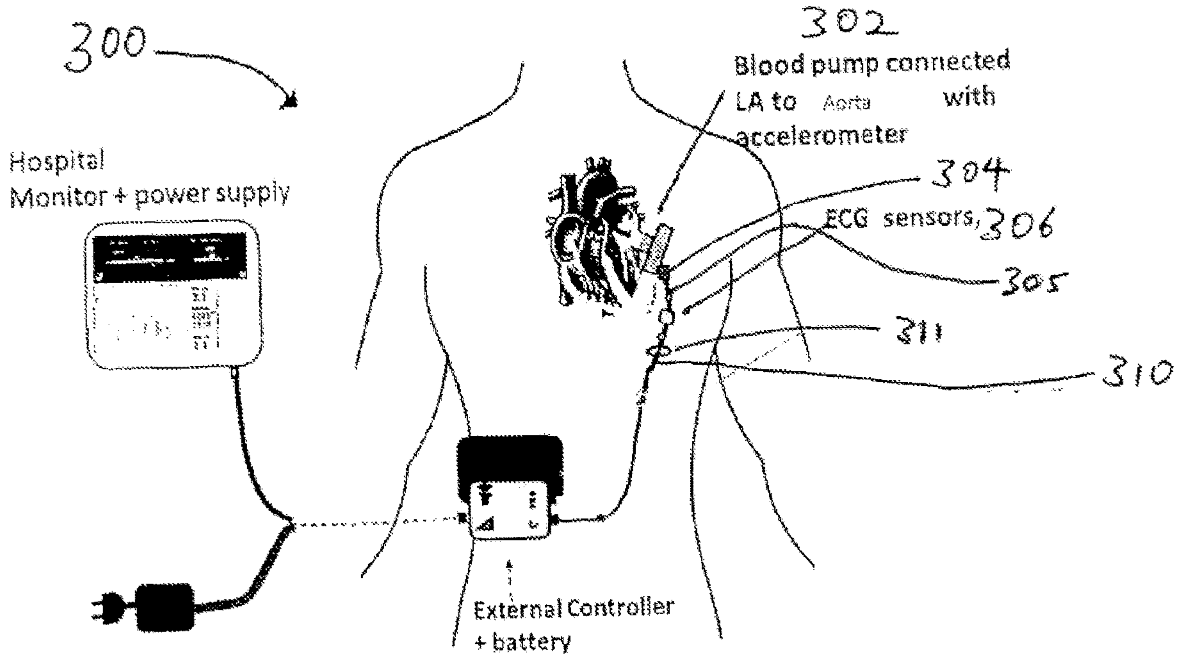
FIG. 10B illustrates another embodiment of an implantable device adapted for assisting the flow of blood from left atrium to an aorta of an in-vivo heart.
Figure 11:
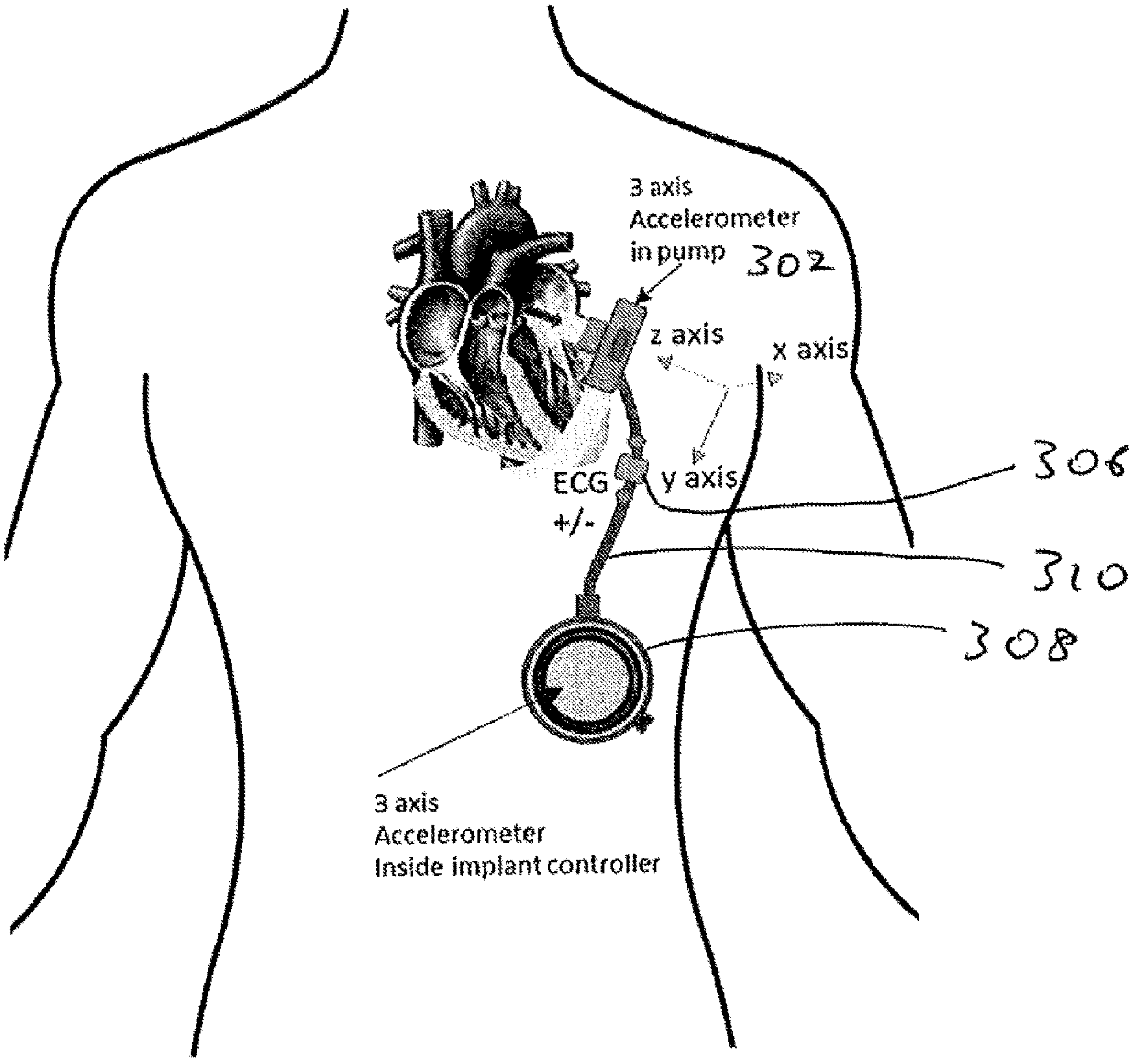
FIG. 11 illustrates another further embodiment of the implantable device as shown in FIG. 10A.

FIGS. 10 and 11 illustrate an embodiment of an implantable device, which may be a blood pump 302, which is mounted or positioned on the Left Atrium (LA) and connects the Left Atrium (LA) to the descending aorta of a patient to allow for pumping of blood from LA to aorta. The blood pump 302 may comprise at least one accelerometer 304 for detecting the patient's posture or orientation by detecting and analysing the shifts in the X, Y, and Z planes and/or average values. The at least one accelerometer 304 may also detect and the patient's physical activity by measuring/calculating the velocity and/or acceleration of the patient. Preferably, the blood pump may be a centrifugal rotary pump wherein the processor in the controller drives the pump using waveform modulation. The controller drives the rotation of an impeller within the pump at a predetermined target speed or velocity as calculated by the controller or processor.

The blood pump 302 may be in electrical communication with an ECG sensor 306. The ECG sensor 306 may be located external to the implanted controller 308 connected by a lead 310 near the heart of a patient. The ECG sensor 306 may be located between the blood pump 302 and the implanted controller 308. There may be the use of at least two electrodes for sensing the ventricular contraction vector across the atrioventricular (AV) plane. The electrode may be constructed of an inert material such as titanium. It may be appreciated that any type of inert material may be suitable for use as an electrode.

Figure 12:
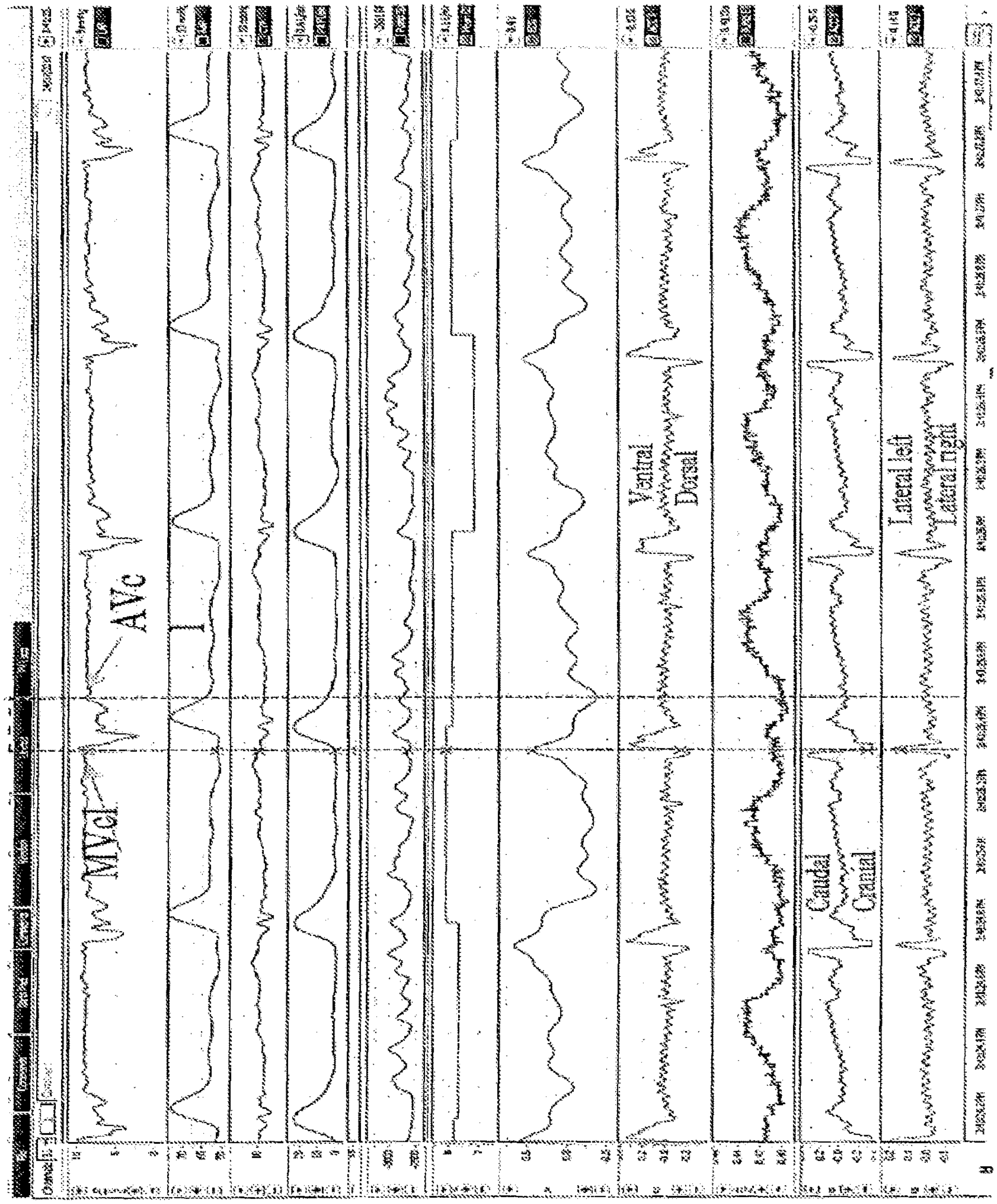
FIG. 12 illustrates a graph of various parameters sensed plotted and aligned with respect to time.

As illustrated in FIGS. 10A and 11, the blood pump 302 may be implanted into a patient such that the inlet cannular protrudes into the left atrium. As the patient's heart contracts and relaxes, normally the valves open and shut, letting blood flow into the ventricles and atria at alternate times. After the left ventricle contracts, the aortic valve closes and the mitral valve opens, to allow blood to flow from the left atrium into the left ventricle. As the left atrium contracts, more blood flows into the left ventricle. When the left ventricle contracts again, the mitral valve closes and the aortic valve opens, so blood flows into the aorta. Normally, the mitral valve and aortic valves open and close respectively throughout the cardiac cycle. The motions are recorded and analysed by the accelerometer 304 with the blood pump 302. FIG. 12 graphically illustrates XYZ accelerometer data collected from a patient's heart with the implanted system running with Mitral valve closure. The intensity of closure may determine a value called MVacc Amplitude which may be representative of the amount of acceleration produced by the mitral valve closing and the shock wave propagating through to the blood pump 302.

The motion of the heart in normal pumping or states such as ventricular fibrillation (VF) or atrial fibrillation (AF) can also be detected using the pump's accelerometer using signal processing techniques such as spectral analysis and wavelet analysis methods.

The patient's heart rate can be detected and/or analysed by interpreting the graph relating to the valve action or the ECG. In the case where the valves fail to open, interpreting the ECG graph is preferred.

Respiration can be detected via the implant controller's 308 internal accelerometer 304 which may be placed on the outside of the chest cavity near the patient's rib cage.

The pump flow rate may be estimated using pump speed and pump input power combined with viscosity or the patient's blood haematocrit (the ratio of the volume of red blood cells to the total volume of blood) which may be inputted by the clinician. A range between 20% to 50% may be inputted by the clinician.

Figure 13:
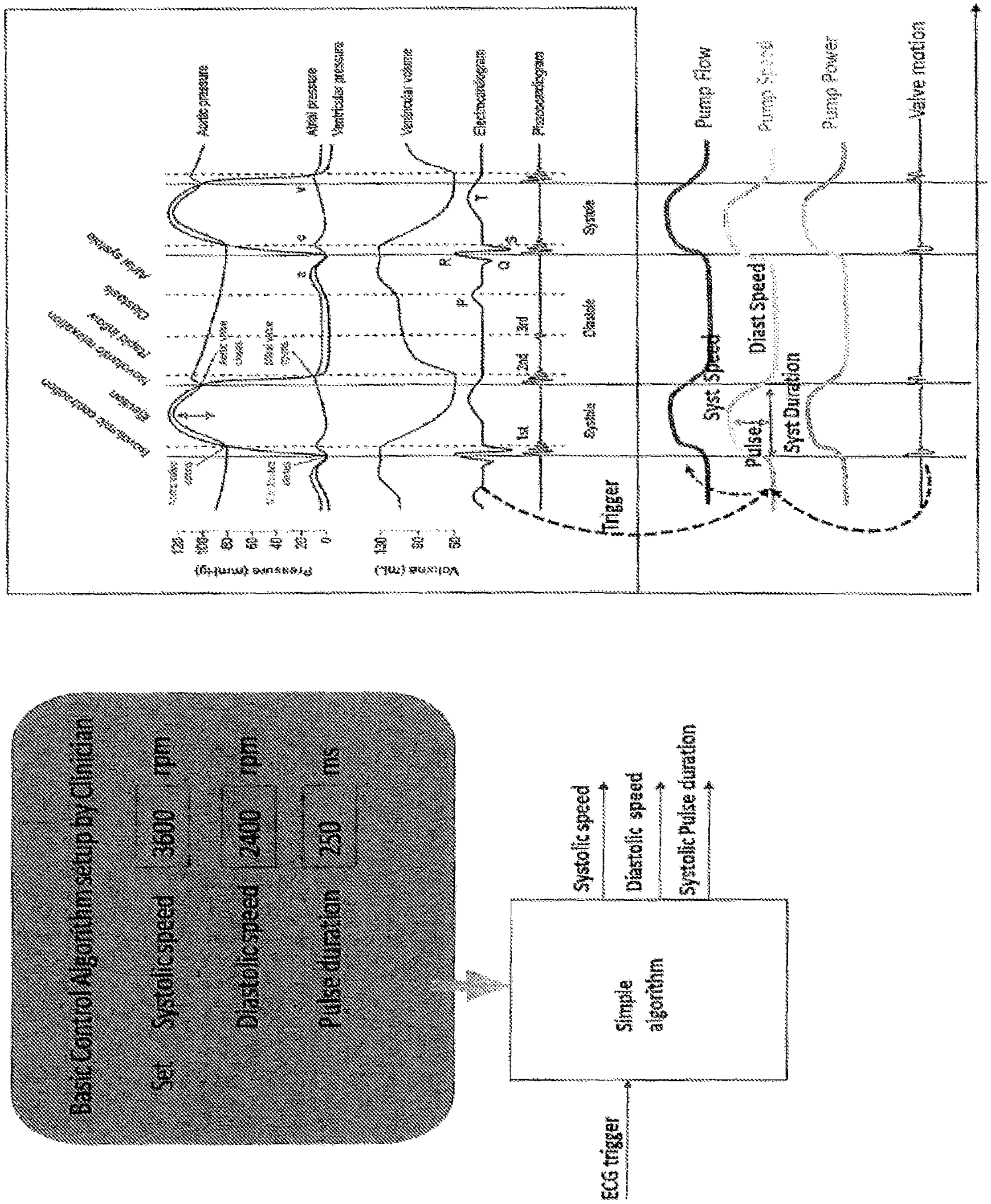
FIG. 13 illustrates a simplified process using a basic algorithm for determining the systolic speed, diastolic speed, and systolic pulse duration from ECG sensor data.

As illustrated in FIG. 13, the basic algorithm may be triggered by sensing the heart's ECG from the system's electrodes and may set the pump speed or target speed for the systolic and diastolic period of the heart as well as the duration of the systolic pump speed. Both these speed set points and duration may be set by the clinician using the hospital monitor software. It may be appreciated that multiple graphical data be considered together to verify or interpret whether the sound of phonocardiogram is the start of the systolic period or the diastolic period. Not limited to the following example of interpretation, an example of interpretation may be reading a record of the sound made by a beating heart, the start of the systolic period may be considered when the ventricular pressure is low or almost zero.

The electrical conduction system of the heart is the interpretation of the ECG. Normal conduction starts and propagates in a predictable pattern, and deviation from this pattern can be a normal variation or be pathological. Ventricular fibrillation produces an ECG but is too dysfunctional to produce a life-sustaining cardiac output. A normal rhythm produces four entities: a P wave, a QRS complex, a T wave, and a U wave, in which each have a unique pattern. The P wave represents atrial depolarization, the QRS complex represents the rapid depolarisation of the right and left ventricles, the T wave represents ventricular repolarisation, and the U wave represents papillary muscle repolarisation.

Where the ECG is detected, the implanted controller 308 may increase the systolic pump speed for a given systolic pulse duration followed by the implanted controller 308 then setting the diastolic pump speed. A low pump flow estimate may be calculated using the data gathered from a combination of the pump's power drawn and the default alarm speed, which may be set by the clinician, the system may set the low pump speed to be low. The pump flow may be estimated or inferred using a combination of the amount of power drawn from the blood pressure pump and from the blood pressure pump speed. If the pump flow estimate inferred by the calculation may be beyond a safe predetermined threshold value, an alarm may sound to alert the clinician and the processor may dynamically operate the blood pressure pump's speed to a predetermined safe blood pressure pump speed according to the determined patient posture and/or patient activity.

Figure 16:
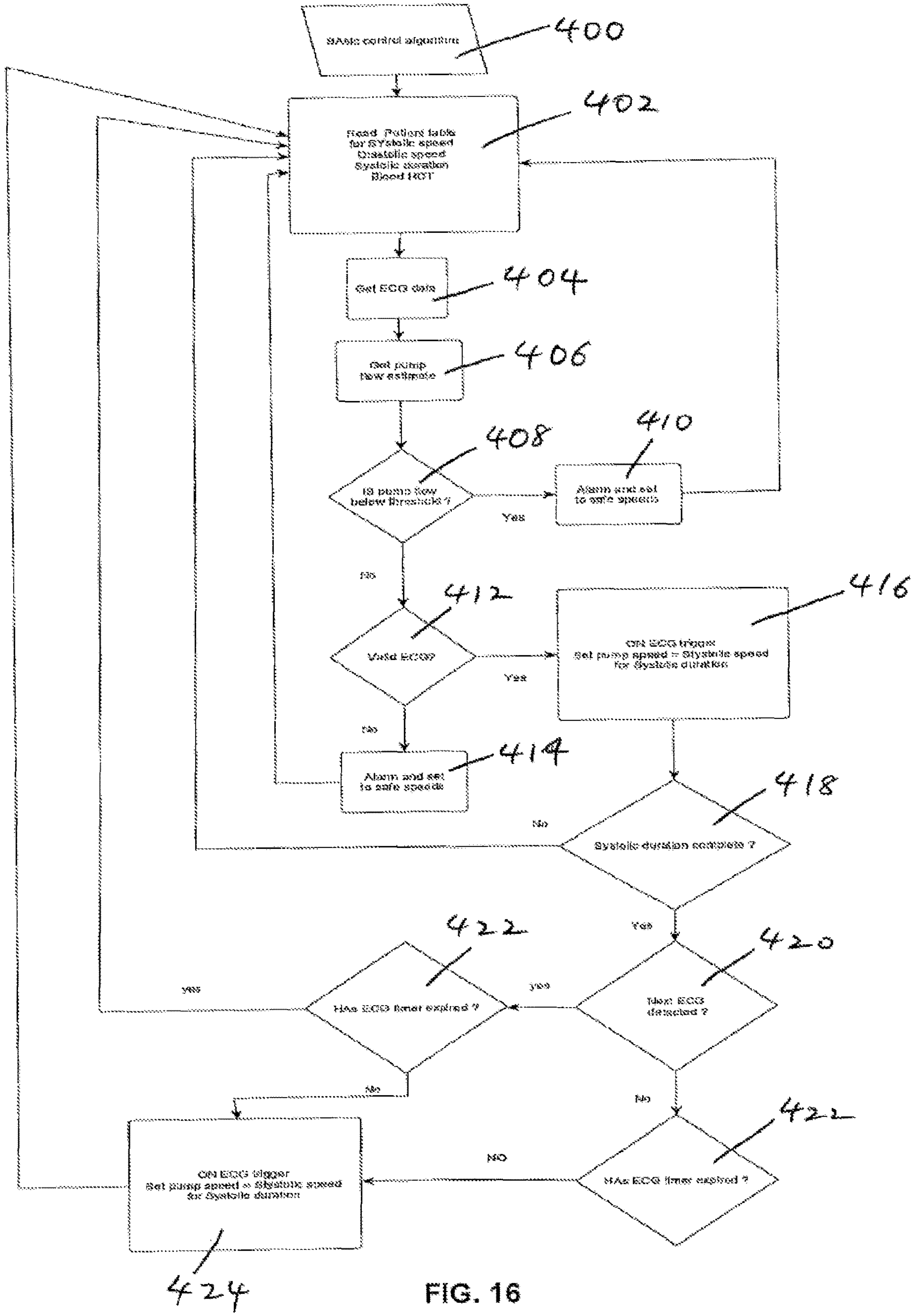
FIG. 16 illustrates a decision flow chart of a basic control algorithm.

As illustrated in FIG. 16, there may be a basic control algorithm 400 for reading patient table for systolic speed, diastolic speed, systolic duration and Blood haematocrit 402. The system may get ECG data 404, followed by getting pump flow estimate 406. Based on the data and calculation, the system then decides whether the pump flow is below a predetermined safe threshold 408. If yes, the system may alarm and may set to pump flow to safe speeds on a default basis followed by checking the steps of 402, 404 and 406 again. When the pump flow is not below a predetermined safe threshold, the system may analyse whether a valid ECG is obtained. If not, the system may also alarm and may set the pump speed to safe speeds 414 and may go back to reading the patient table 402 until a valid ECG is obtained. Once a valid ECG is obtained, it triggers the pump to set a systolic speed for a systolic duration 416. The system then checks whether the duration is complete 418. If not, the system may go back to reading the patient table 402 and follow the sequence accordingly until the systolic duration is complete 418. Once the systolic duration is complete 418, the system then checks whether the next ECG has been detected 420. Regardless of the answer for next ECG detected 420, the system then checks whether the timer for the ECG has expired 422. If yes, the system may go back to reading the patient table 402. If the ECG timer has not expired 422, it triggers the pump to set a systolic speed for a systolic duration 424. The system then continually goes back and reading the patient table 402 again so that safe pump speeds can be continually operated by the blood pump.

Figure 14:
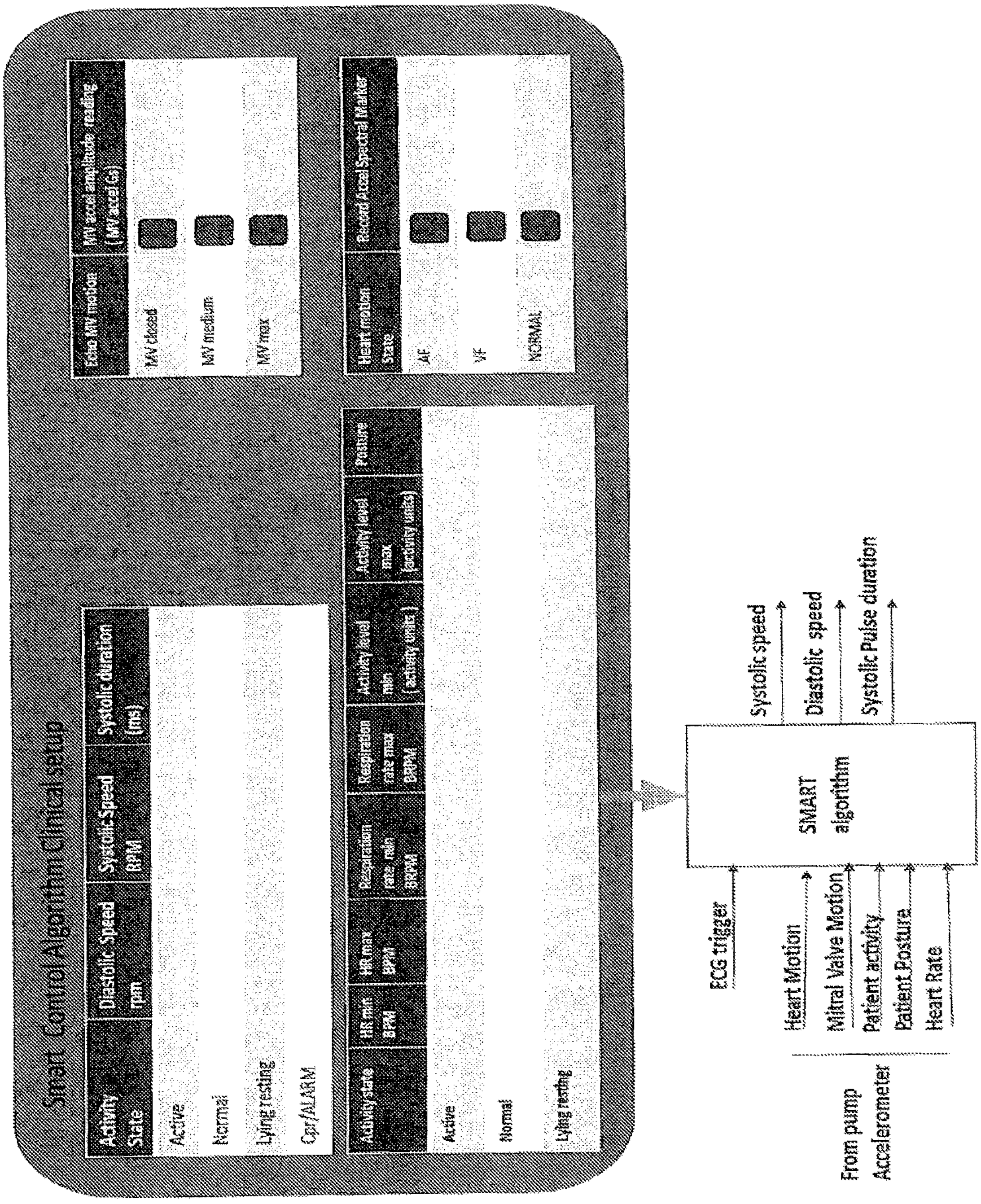
FIG. 14 illustrates another simplified process using an improved algorithm for determining the systolic speed, diastolic speed and systolic pulse duration; from considering various physiological parameters.
Figure 17:
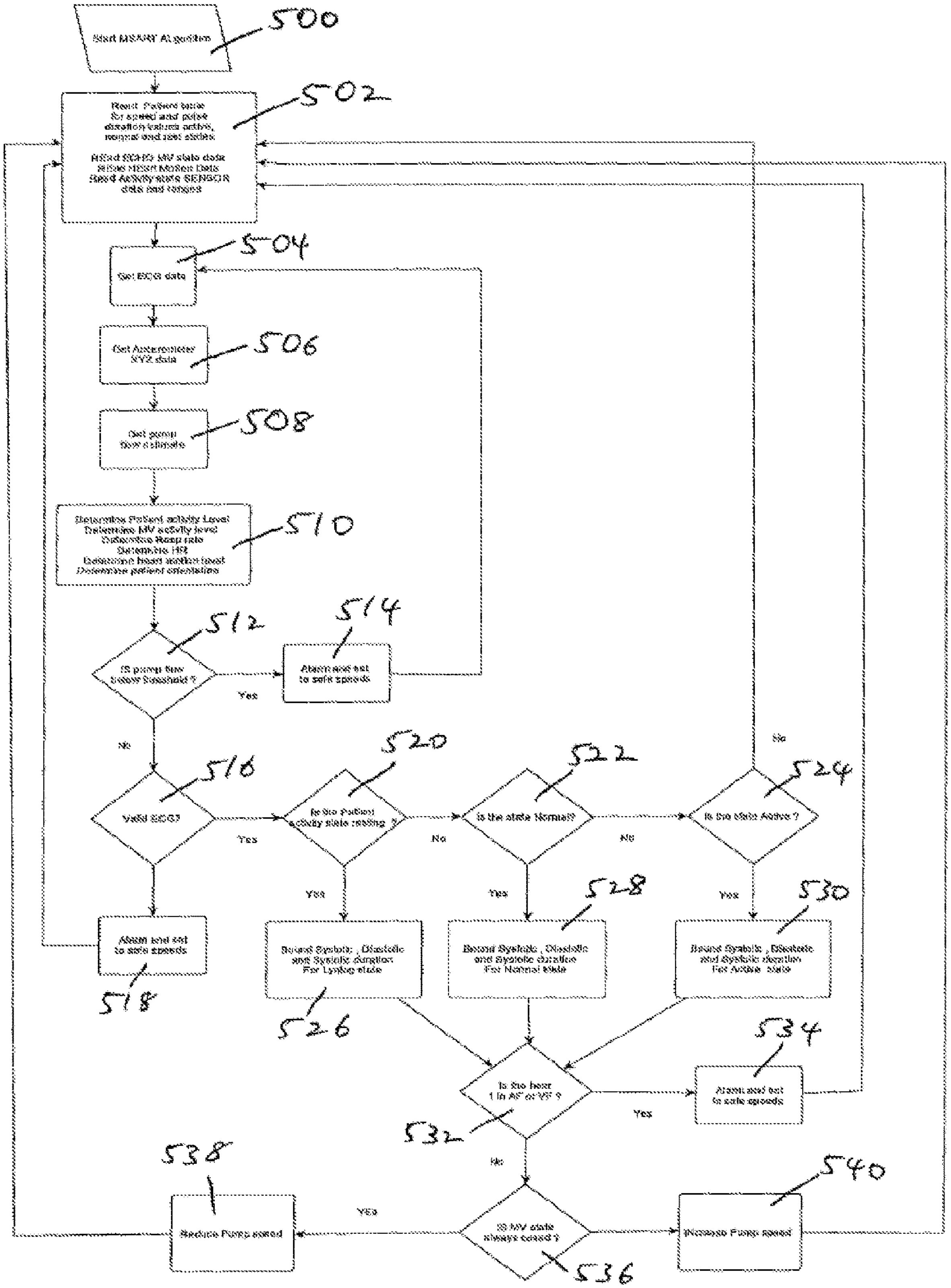
FIG. 17 illustrates a decision flow chart of an improved algorithm.

As illustrated in FIG. 17, there may be an improved or smart algorithm 500 for setting the blood pressure pump's systolic speed, diastolic speed and systolic pulse duration. The clinician may set the predetermined blood pressure pump's safety speed limit relating to these parameters. The smart algorithm may utilise data from a variety of different physiological parameters and a group of sensor inputs to automatically and dynamically adjust the pump output suitable to the unique lifestyle for each patient. For example, the clinician may use the data/information displayed in the Smart Control Algorithm Clinical table as shown in FIG. 14 and depending on the data or results in the Smart Control Algorithm Clinical table, the smart algorithm then optimally calculate or determine the systolic blood pressure pumping speed, diastolic blood pressure pumping speed, and the systolic pulse duration.

Once the Left Ventricle Assist Device has been implanted, data relating to the physiological parameters may be gathered. The gathered data may be displayed on an external hospital monitor interface, in which the external hospital monitor interface may comprise software for communicating with and/or operating the device. The device may use an external doppler ECHO to examine the heart, in which the echocardiogram may use high frequency sound waves to create an image of the heart while the use of Doppler technology allows the determination of the speed and direction of blood flow through using the Doppler effect. The advantage of Doppler echocardiography is that it can be used to measure blood flow within the heart without invasive procedures such as cardiac catheterisation. The mitral valve of the patient's heart may be imaged in real time using this method and therefore the periodic movement of the mitral valve may be imaged with respect to time. Depending on the type of movement of the mitral valve or lack of movement of the mitral valve, the blood pressure pump speed may be varied such there is a periodic movement of the mitral valve for allowing blood to flow from the left atrium to the left ventricle of the patient's heart. For each patient's activity state and posture, the variable mitral valve amplitude may be recorded by the system by the clinician. A snapshot value will be automatically shown in the table for that state in the moment of time of analysis. Furthermore, clinicians may characterise heart motions in a similar way using the ECHO technique or using standard medical diagnostics.

The improved or smart algorithm may first consider data from the patient table, speed and pulse duration; as well as considering from the accelerometer data whether the patient is in which activity state and/or which posture 502; as well as considering the following data: ECHO Mitral Valve state data, heart motion data and activity state sensor data and ranges. The processor may then get ECG data 504, followed by accelerometer XYZ coordinate data 506, followed by pump flow estimate data 508. Following obtaining the data of 502, 504, 506, 508, the processor may then determine the patient activity level, mitral valve activity level, respiration rate, heart rate, heart motion level, and patient orientation 510. The processor then considers whether the current blood pressure pump flow is below the safe threshold 512. If yes, the processor may then alert or alarm and may set the blood pressure pump to default safe speeds 514. The system then repeats obtaining the data 504, 506, 508, and 510 until the blood pressure pump flow is within a safe threshold 512. Once the pump flow is within a safe threshold, the processor then obtains ECG data 516 and may determine whether it is valid. If not, the processor may alert/alarm and may set the pump speed to the safe threshold speed 518 followed by considering the data from 502 to 512 and 516 again until a valid ECG 516 is obtained. Then the system considers whether the patient activity state is 'resting'/'lying' 520, or 'normal' 522, or 'active' 524, in which each of the activity states 520, 522, 524 has its own respective predetermined systolic speed, diastolic speed and systolic pulse duration 526, 528, 530.

If HR range=LYING HR range AND respiration rate=LYING RR range and activity level=LYING activity range AND posture=RESTING THEN Activity state=RESTING If HR range=NORMAL HR range AND respiration rate=NORMAL RR range and activity level=NORMAL activity range AND posture=NORMAL THEN Activity state=NORMAL If HR range=ACTIVE HR range AND respiration rate=ACTIVE RR range and activity level=ACTIVE activity range AND posture=ACTIVE THEN Activity state=ACTIVE If posture=RESTING (Zone 1) And HR range=Low HR (zone 1) range AND respiration rate=LYING RR range (zone 1). THEN: Activity state=RESTING (zone 1+1+1+1)

If posture=NORMAL (zone 2) and HR range=NORMAL HR range (zone 2) AND respiration rate=NORMAL RR range (zone 2) THEN Activity state=NORMAL (zone 2+2+2+2)

If posture=ACTIVE (zone 3) and HR range=ACTIVE HR range (Zone 3) AND respiration rate=ACTIVE RR range (zone 3) THEN Activity state=ACTIVE (zone 3+3+3+3)

Position will be the superior variable before HR and Respiration. If one of the parameters is in a lower range, that is, HR active (zone 3), Respiration=active (zone 3) and posture=resting (zone 1), then the lower variable will determine the state of the program=Zone 1 mode.

| | Zone 1 | Zone 2 | Zone 3 |
|---|---|---|---|
| Position | 1 | 2 | 3 |
| HR | 1 | 2 | 3 |
| Respiration | 1 | 2 | 3 |
| THEN | 1 | 2 | 3 |

The above variables may be input by the clinician and may be fine tuned for each patient. These states may allow the system to change the bounded limits set by the clinician automatically. It may create a table which shows that if position is 1, HR is 2 and RESP is 2, it is still Zone 1, for example as part of the safety algorithm or calculation.

If the processor cannot determine whether the patient activity state is any one of resting, normal or active, the processor checks back from 502 until the patient activity state is determined.

The above variables may be inputted by the clinician and depending on the lifestyle of the patient, the above variables may be fine-tuned for each patient. Determination of the state of the patient may allow the device to dynamically change the predetermined limits set by the clinician.

The analysis of the patient's activity state may be combined with the Mitral Valve activity value (MVaccel amplitude) to find the optimal pumping speed for the patient while the pumping speed may be bounded by the safe pumping speed output set so that within each activity state the controller may automatically adjust pump speeds Once the determined patient activity state has been determined and the associated speed and duration for the blood pressure pump is operated, the processor then decides whether the heart is in Atrial Fibrillation (AF) or Ventricular Fibrillation (VF) 532. If it is either Atrial Fibrillation or Ventricular Fibrillation, the system may alert or alarm and set the blood pressure pump to a safe predetermined speed 534 followed by checking back from 502 until the heart is not in Atrial Fibrillation or Ventricular Fibrillation anymore. The processor then considers whether the pump speed renders the mitral valve to be always closed 536. If it is always closed, then the processor may reduce the pump speed 540 to a speed that the mitral valve is not always closed 536. It may be appreciated that while the pump speed may not always close the mitral valve, the pump speed may be increased 540 such that pump speed may be as close towards the optimal pump speed as possible for the patient's activity state at the time. It may be advantageous to use a smart algorithm taking into account various physiological parameters or data so that the pump speed can be operated at a predetermined safe speed and/or optimal for the patient's activity state. As it is appreciated that different patient activity states and patient postures have different pumping safe speed requirements, the smart algorithm may operate the blood pressure pump more accurately compared to a basic algorithm. Preferably, the mitral valve may be openable during a periodic cardiac cycle. If mitral valve opening time may be decreased, aortic flow may be decreased and cerebral flow may be decreased by the reduction of pressure from the left atrium. The movement of the aortic valve and/or mitral valve may be shown on the hospital monitor such that the physician or clinician can see that aortic valve open during the systole and the mitral valve open during the diastole. The smart or improved algorithm may take into account that as the mitral valve opening time reduces, the rpm should be reduced. Similarly, the smart or improved algorithm may take into account that as the aortic valve opening time reduces, the rpm should be reduced. It may be appreciated that noise may interfere with the mitral valve movements however, the noise may be filtered out such that the mitral valve movement can be accurately represented.

Figure 15:
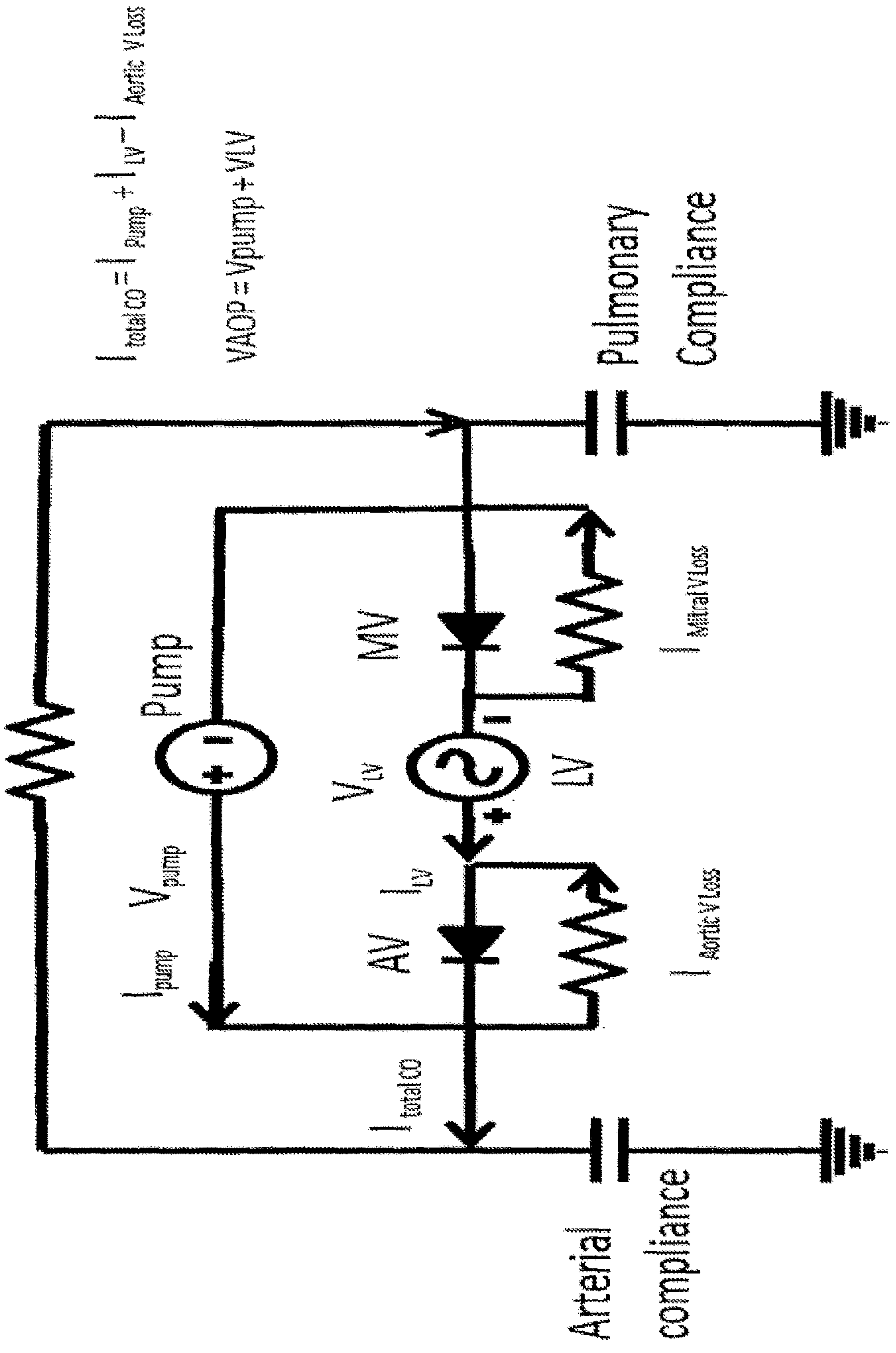
FIG. 15 illustrates a circuit diagram for measuring the current of the total cardiac output ($I_{total\ CO}$).

FIG. 15 illustrates a circuit model for the device, in which the blood pressure pump may be in parallel to the left ventricle removing blood from the left atrium. By connecting in parallel, rather than in series, the blood pumping state may be detectable from this circuit model. If the mitral valve is not opening over the cardiac cycle, this may mean that the blood pump may be pumping all the blood to the aorta or there may be suction or over pumping of the blood in the left atrium. Exclusively, small leakages in the heart valves may be determined by the detection of resistances across the diodes. Suction in the left atrium may be indicated by a low or erratic estimated pump flow rate. However, if the Mitral Valve is not opening over the cardiac cycle and there is no suction, this may mean that the blood pressure pump may be delivering all flow to the descending aorta and may be beyond the optimal set point. The controller may then reduce the blood pressure pump speed and the blood may then flow in small steps such that the mitral valve may open in the cardiac cycle while not exceeding safe the pump flow rate set with respect to the patient's posture and activity. If the mitral value is opening then the pump speed may be increased or decreased in small steps and monitoring the MVaccel amplitude value until the optimal pump speed is reached.

In another embodiment, the implantable pump may have an internal controller that may operate on a basic algorithm if the external controller may not be connected. The internal controller may only be programmed without the improved or smart algorithm. The internal controller may house a battery or electric source such as a shower battery. The internal controller may be powered by a transcutaneous energy system for short term use. The external controller may be programmable to have smart function algorithms for responding to patient physical demands or patient posture and activity states. There may be a hospital monitor to program the patient's internal and external controllers.

In yet another embodiment, the ECG electrodes may be connected to the drive line following the heart outside the pericardium. By sensing the heart's ECG from the system's electrodes, variables are programmed to set the pump speed for the systolic and diastolic period of the heart as well as the duration of the systolic pump speed. The first accelerometer may be integrated in the pump, in which the first accelerometer may describe the XYZ position of the patient including the patient's movements and respiration. The blood pump may be implanted such that the inlet cannula protrude into the left atrium and as the heart contract, the aortic valve may open with the mitral valve already closed throughout the cardiac cycle. This motion may be imprinted on the accelerometer within the pump. The intensity of closure may determine a value called MVacc Amplitude which may be representative of the amount of acceleration produced by the mitral valve closing and the shock wave propagating through to the pump as shown in FIG. 11.

For the Basic Algorithm, atrial unloading may be done in systole when the mitral valve is closed and atrial filling happens. A baseline rpm may be set for the diastole with minimal unloading to prevent reverse flow through the blood pressure pump. In the systole, the rpm may be increased. With reference to FIG. 13, the basic algorithm may be triggered by sensing the heart's ECG from the systems electrodes and may set the pump speed for the systolic and diastolic period of the heart as well as the duration for the increased systolic pump speed. Both these speed set points and duration may be set by the clinician using the hospital monitor software, systemic BP, ECHO and clinical evaluation. Information may also be collected from ECG, accelerometers, estimated blood flow.

In another embodiment of present invention, an implanted controller may be adapted for driving a centrifugal implanted blood pump, wherein the pump is connected between left atrium to aorta and is driven at predetermined target speed by the controller. The controller may detect mitral valve motion and may amend target speed to maximise target speed wherein the mitral valve motion is periodic during cardiac cycle and wherein the target speed is above a calculated minimum target speed. The controller may detect posture and activity of user of the pump and may calculate the minimum target speed. The implanted may classify posture and activity as one of three predetermined states which may be lying/resting, normal, or active. The controller may also selectively fluctuate target speed between maximised target speed and minimum target speed to replicate cardiac cycle.

FIG. 10B illustrate another preferred embodiment of an implantable device, which may be an implantable blood pump 302, which is mounted or positioned on the Left Atrium (LA) and connects the Left Atrium (LA) to the descending aorta of a patient to allow for pumping of blood from LA to any aorta depending on the connection of the inlet cannula and the outlet cannula. That is, for example, an inlet cannula is adapted to be connected to the left atrium and an outlet cannula adapted to be connected to an aorta. In other preferred embodiments depending on preferred blood flow routes, the blood pump 302 which is mounted or positioned on the left atrium (LA) and connects the Left Atrium (LA) to the subclavian aorta or arteries of a patient. It may be appreciated that the different routes can be connected between the left atrium (LA) and to any aorta depending on where the outlet cannula is connected to.

The blood pump 302 may comprise at least one accelerometer 304 for detecting the patient's posture or orientation by detecting and analysing the shifts in the X, Y, and Z planes and/or average values. The at least one accelerometer 304 may also detect and the patient's physical activity by measuring/calculating the velocity and/or acceleration of the patient. Preferably, the blood pump may be a centrifugal rotary pump wherein the processor in the controller drives the pump using waveform modulation. The controller drives the rotation of an impeller within the pump at a predetermined target speed or velocity as calculated by the controller or processor.

The blood pump 302 may be in electrical communication with an ECG sensor 306 via a first electrical lead 305. The first electrical lead 305 may comprise a second accelerometer (not shown). The incorporation of the second accelerometer into an electrical lead allows the advantageous sensing capabilities to be integrated directly into the electrical system or cable. This integration can provide valuable data about motion, orientation, or vibrations affecting the system. The second accelerometer may be a very small accelerometer that can fit inside or along the electrical lead 305. This second accelerometer may be a micro-electromechanical system which can be ideal due to their compact size, and low power consumption. This second accelerometer may in one embodiment, fit within the insulation of the electrical lead or cable 305 and in another embodiment, this accelerometer may be attached to the electrical lead's exterior without significantly altering the lead's flexibility or functionality. For the accelerometer being disposed exterior to the lead, it may further require electrical isolation or a non-conductive sheath that can be electrically isolated from the conductive parts of the lead to prevent electrical interference or damage. It may be preferable to provide electromagnetic interference shielding to the accelerometer and filtering algorithms so the electrical lead's current can minimise the affect of the accelerometer's readings. The data transmission of the second accelerometer can use a conductor from the electrical lead 305.

Using accelerometers both at the blood pump 302 and along the electrical lead 305 such as a ventricular assist device (VAD) offers plenty of advantages. This configuration of using a first accelerometer and a second accelerometer can enhance monitoring, diagnostic capabilities, and the overall safety and effectiveness of the device. The advantage of improved operational safety through using more than one accelerometer can advantageously provide early warning systems where variations in vibration patterns detected by either accelerometer can serve as an early warning system for different types of failures, whether they are mechanical, in the case of the blood pump 302, or electrical, along the lead. This allows for proactive measures to prevent harm to the patient. Furthermore, having dual confirmation from having two points of monitoring, such as at the blood pump 302 and the electrical lead 305 allows for advantageous cross-verification of data and thereby increases the reliability of any alerts or diagnostics. Anomalies detected by both accelerometers can confirm the presence of a problem, and reduces false positives. Other advantages can include the optimisation of performance which allows data from each of the accelerometers can be used as a feedback loop for calibration or can be used to fine-tune the operation of the blood pump 302.

The ECG sensor 306 may be located between the blood pump 302 and the external controller 309 connected by a lead 310 near the heart of a patient, in which the lead 310 may be through the skin of the patient at the interface 311. The lead 310 may have a textured silicon polymer surface that is designed to reduce bacterial adhesion and bacterial biofilm formation. By carefully designing the texture of the silicon polymer surface, it is found to be advantageous to inhibit bacterial growth without relying solely on antimicrobial coatings or chemical treatment of the external surface of the lead 310. Another advantage of using the silicon polymer is that the lead 310 or cable 310 that connect the implantable pump 302 to the external controller 309 is that it can withstand constant movement of the patient and flexing without degrading the material or breaking the material. The textured surface can advantageously enhance the mechanical properties of the silicon polymers which makes them more resistant to wear and tear while maintaining or even improving their flexibility. As the lead 310 interfaces with the skin of the patient, such as where the lead 310 or cable exiting the body, a textured surface, or more particularly, a nano-textured surface of the lead 310 can promote better integration with the surrounding tissue and facilitate healing. As human tissue can adaptably heal and seal at the interface, this is advantageous for minimising complications at the exit site.

The ECG sensor 306 may be located internally between the blood pump 302 and the external controller 309. There may be the use of at least two electrodes for sensing the ventricular contraction vector across the atrioventricular (AV) plane. The electrode may be constructed of an inert material such as titanium. It may be appreciated that any type of inert material may be suitable for use as an electrode.

As illustrated in FIGS. 10 and 11, the blood pump 302 may be implanted into a patient such that the inlet cannular protrudes into the left atrium. As the patient's heart contracts and relaxes, normally the valves open and shut, letting blood flow into the ventricles and atria at alternate times. After the left ventricle contracts, the aortic valve closes and the mitral valve opens, to allow blood to flow from the left atrium into the left ventricle. As the left atrium contracts, more blood flows into the left ventricle. When the left ventricle contracts again, the mitral valve closes and the aortic valve opens, so blood flows into the aorta. Normally, the mitral valve and aortic valves open and close respectively throughout the cardiac cycle. The motions are recorded and analysed by the accelerometer 304 with the blood pump 302. While the preferred embodiment uses external controllers, it can similarly collect data if the controller was internal, which can be similarly depicted in FIG. 12, which graphically illustrates XYZ accelerometer data collected from a patient's heart with the implanted system running with Mitral valve closure. The intensity of closure may determine a value called MVacc Amplitude which may be representative of the amount of acceleration produced by the mitral valve closing and the shock wave propagating through to the blood pump 302.

The motion of the heart in normal pumping or states such as ventricular fibrillation (VF) or atrial fibrillation (AF) can also be detected using the pump's accelerometer using signal processing techniques such as spectral analysis and wavelet analysis methods.

The patient's heart rate can be detected and/or analysed by interpreting the graph relating to the valve action or the ECG. In the case where the valves fail to open, interpreting the ECG graph is preferred.

Respiration can be detected via the second accelerometer, which may be placed proximal of the chest cavity near the patient's rib cage. Respiration can be detected through body movement from expansion and contraction of the chest and abdomen as the lungs fill with air then emptied. These movements cause slight but detectable shifts in the body's position and orientation, which can be sensed by the accelerometer. By analysing the patterns and frequencies of these signals, the software algorithms can differentiate between various types of movement and identify those specially associated with breathing. When synchronising with breathing, this implantable device can mimic the natural response of the heart as closely as possible, including varying the output based on the body's changing needs. Respiratory rate and depth can provide advantageous insights into the patient's immediate circulatory requirements and may dynamically allow the implanted blood pump to adjust its pumping action in a physiologically compatible manner.

The pump flow rate may be estimated using pump speed and pump input power combined with viscosity or the patient's blood haematocrit (the ratio of the volume of red blood cells to the total volume of blood) which may be inputted by the clinician. A range between 20% to 50% may be inputted by the clinician.

While for this preferred embodiment of the controller being external, it can similarly operate similar to the previous embodiment described using an internal controller and an external controller. As illustrated in FIG. 13, the basic algorithm may be triggered by sensing the heart's ECG from the system's electrodes and may set the pump speed or target speed for the systolic and diastolic period of the heart as well as the duration of the systolic pump speed. Both these speed set points and duration may be set by the clinician using the hospital monitor software. It may be appreciated that multiple graphical data be considered together to verify or interpret whether the sound of phonocardiogram is the start of the systolic period or the diastolic period. Not limited to the following example of interpretation, an example of interpretation may be reading a record of the sound made by a beating heart, the start of the systolic period may be considered when the ventricular pressure is low or almost zero.

The electrical conduction system of the heart is the interpretation of the ECG. Normal conduction starts and propagates in a predictable pattern, and deviation from this pattern can be a normal variation or be pathological. Ventricular fibrillation produces an ECG but is too dysfunctional to produce a life-sustaining cardiac output. A normal rhythm produces four entities: a P wave, a QRS complex, a T wave, and a U wave, in which each have a unique pattern. The P wave represents atrial depolarization, the QRS complex represents the rapid depolarisation of the right and left ventricles, the T wave represents ventricular repolarisation, and the U wave represents papillary muscle repolarisation.

Where the ECG is detected, the external controller 309 may increase the systolic pump speed for a given systolic pulse duration followed by the external controller 309 then setting the diastolic pump speed. A low pump flow estimate may be calculated using the data gathered from a combination of the pump's power drawn and the default alarm speed, which may be set by the clinician, the system may set the low pump speed to be low. The pump flow may be estimated or inferred using a combination of the amount of power drawn from the blood pressure pump and from the blood pressure pump speed. If the pump flow estimate inferred by the calculation may be beyond a safe predetermined threshold value, an alarm may sound to alert the clinician and the processor may dynamically operate the blood pressure pump's speed to a predetermined safe blood pressure pump speed according to the determined patient posture and/or patient activity.

As illustrated in FIG. 16, there may be a basic control algorithm 400 for reading patient table for systolic speed, diastolic speed, systolic duration and Blood haematocrit 402 as used for the preferred embodiment of the controllers being external. The system may get ECG data 404, followed by getting pump flow estimate 406. Based on the data and calculation, the system then decides whether the pump flow is below a predetermined safe threshold 408. If yes, the system may alarm and may set to pump flow to safe speeds on a default basis followed by checking the steps of 402, 404 and 406 again. When the pump flow is not below a predetermined safe threshold, the system may analyse whether a valid ECG is obtained. If not, the system may also alarm and may set the pump speed to safe speeds 414 and may go back to reading the patient table 402 until a valid ECG is obtained. Once a valid ECG is obtained, it triggers the pump to set a systolic speed for a systolic duration 416. The system then checks whether the duration is complete 418. If not, the system may go back to reading the patient table 402 and follow the sequence accordingly until the systolic duration is complete 418. Once the systolic duration is complete 418, the system then checks whether the next ECG has been detected 420. Regardless of the answer for next ECG detected 420, the system then checks whether the timer for the ECG has expired 422. If yes, the system may go back to reading the patient table 402. If the ECG timer has not expired 422, it triggers the pump to set a systolic speed for a systolic duration 424. The system then continually goes back and reading the patient table 402 again so that safe pump speeds can be continually operated by the blood pump.

As illustrated in FIG. 17, there may be an improved or smart algorithm 500 for setting the blood pressure pump's systolic speed, diastolic speed and systolic pulse duration. The clinician may set the predetermined blood pressure pump's safety speed limit relating to these parameters. The smart algorithm may utilise data from a variety of different physiological parameters and a group of sensor inputs to automatically and dynamically adjust the pump output suitable to the unique lifestyle for each patient. For example, the clinician may use the data/information displayed in the Smart Control Algorithm Clinical table as shown in FIG. 14 and depending on the data or results in the Smart Control Algorithm Clinical table, the smart algorithm then optimally calculate or determine the systolic blood pressure pumping speed, diastolic blood pressure pumping speed, and the systolic pulse duration.

Once the Left Ventricle Assist Device has been implanted, data relating to the physiological parameters may be gathered. The gathered data may be displayed on an external hospital monitor interface, in which the external hospital monitor interface may comprise software for communicating with and/or operating the device. The device may use an external doppler ECHO to examine the heart, in which the echocardiogram may use high frequency sound waves to create an image of the heart while the use of Doppler technology allows the determination of the speed and direction of blood flow through using the Doppler effect. The advantage of Doppler echocardiography is that it can be used to measure blood flow within the heart without invasive procedures such as cardiac catheterisation. The mitral valve of the patient's heart may be imaged in real time using this method and therefore the periodic movement of the mitral valve may be imaged with respect to time. Depending on the type of movement of the mitral valve or lack of movement of the mitral valve, the blood pressure pump speed may be varied such there is a periodic movement of the mitral valve for allowing blood to flow from the left atrium to the left ventricle of the patient's heart. For each patient's activity state and posture, the variable mitral valve amplitude may be recorded by the system by the clinician. A snapshot value will be automatically shown in the table for that state in the moment of time of analysis. Furthermore, clinicians may characterise heart motions in a similar way using the ECHO technique or using standard medical diagnostics.

The improved or smart algorithm may first consider data from the patient table, speed and pulse duration; as well as considering from the accelerometer data whether the patient is in which activity state and/or which posture 502; as well as considering the following data: ECHO Mitral Valve state data, heart motion data and activity state sensor data and ranges. The processor may then get ECG data 504, followed by accelerometer XYZ coordinate data 506, followed by pump flow estimate data 508. Following obtaining the data of 502, 504, 506, 508, the processor may then determine the patient activity level, mitral valve activity level, respiration rate, heart rate, heart motion level, and patient orientation 510. The processor then considers whether the current blood pressure pump flow is below the safe threshold 512. If yes, the processor may then alert or alarm and may set the blood pressure pump to default safe speeds 514. The system then repeats obtaining the data 504, 506, 508, and 510 until the blood pressure pump flow is within a safe threshold 512. Once the pump flow is within a safe threshold, the processor then obtains ECG data 516 and may determine whether it is valid. If not, the processor may alert/alarm and may set the pump speed to the safe threshold speed 518 followed by considering the data from 502 to 512 and 516 again until a valid ECG 516 is obtained. Then the system considers whether the patient activity state is 'resting'/'lying' 520, or 'normal' 522, or 'active' 524, in which each of the activity states 520, 522, 524 has its own respective predetermined systolic speed, diastolic speed and systolic pulse duration 526, 528, 530.

If HR range=LYING HR range AND respiration rate=LYING RR range and activity level=LYING activity range AND posture=RESTING THEN Activity state=RESTING If HR range=NORMAL HR range AND respiration rate=NORMAL RR range and activity level=NORMAL activity range AND posture=NORMAL THEN Activity state=NORMAL If HR range=ACTIVE HR range AND respiration rate=ACTIVE RR range and activity level=ACTIVE activity range AND posture=ACTIVE THEN Activity state=ACTIVE If posture=RESTING (Zone 1) And HR range=Low HR (zone 1) range AND respiration rate=LYING RR range (zone 1). THEN: Activity state=RESTING (zone 1+1+1+1)

If posture=NORMAL (zone 2) and HR range=NORMAL HR range (zone 2) AND respiration rate=NORMAL RR range (zone 2) THEN Activity state=NORMAL (zone 2+2+2+2)

If posture=ACTIVE (zone 3) and HR range=ACTIVE HR range (Zone 3) AND respiration rate=ACTIVE RR range (zone 3) THEN Activity state=ACTIVE (zone 3+3+3+3)

Position will be the superior variable before HR and Respiration. If one of the parameters is in a lower range, that is, HR active (zone 3), Respiration=active (zone 3) and posture=resting (zone 1), then the lower variable will determine the state of the program=Zone 1 mode.

| | Zone 1 | Zone 2 | Zone 3 |
|---|---|---|---|
| Position | 1 | 2 | 3 |
| HR | 1 | 2 | 3 |
| Respiration | 1 | 2 | 3 |
| THEN | 1 | 2 | 3 |

The above variables may be input by the clinician and may be fine tuned for each patient. These states may allow the system to change the bounded limits set by the clinician automatically. It may create a table which shows that if position is 1, HR is 2 and RESP is 2, it is still Zone 1, for example as part of the safety algorithm or calculation.

If the processor cannot determine whether the patient activity state is any one of resting, normal or active, the processor checks back from 502 until the patient activity state is determined.

The above variables may be inputted by the clinician and depending on the lifestyle of the patient, the above variables may be fine-tuned for each patient. Determination of the state of the patient may allow the device to dynamically change the predetermined limits set by the clinician.

The analysis of the patient's activity state may be combined with the Mitral Valve activity value (MVaccel amplitude) to find the optimal pumping speed for the patient while the pumping speed may be bounded by the safe pumping speed output set so that within each activity state the controller may automatically adjust pump speeds Once the determined patient activity state has been determined and the associated speed and duration for the blood pressure pump is operated, the processor then decides whether the heart is in Atrial Fibrillation (AF) or Ventricular Fibrillation (VF) 532. If it is either Atrial Fibrillation or Ventricular Fibrillation, the system may alert or alarm and set the blood pressure pump to a safe predetermined speed 534 followed by checking back from 502 until the heart is not in Atrial Fibrillation or Ventricular Fibrillation anymore. The processor then considers whether the pump speed renders the mitral valve to be always closed 536. If it is always closed, then the processor may reduce the pump speed 540 to a speed that the mitral valve is not always closed 536. It may be appreciated that while the pump speed may not always close the mitral valve, the pump speed may be increased 540 such that pump speed may be as close towards the optimal pump speed as possible for the patient's activity state at the time. It may be advantageous to use a smart algorithm taking into account various physiological parameters or data so that the pump speed can be operated at a predetermined safe speed and/or optimal for the patient's activity state. As it is appreciated that different patient activity states and patient postures have different pumping safe speed requirements, the smart algorithm may operate the blood pressure pump more accurately compared to a basic algorithm. Preferably, the mitral valve may be openable during a periodic cardiac cycle. If mitral valve opening time may be decreased, aortic flow may be decreased and cerebral flow may be decreased by the reduction of pressure from the left atrium. The movement of the aortic valve and/or mitral valve may be shown on the hospital monitor such that the physician or clinician can see that aortic valve open during the systole and the mitral valve open during the diastole. The smart or improved algorithm may take into account that as the mitral valve opening time reduces, the rpm should be reduced. Similarly, the smart or improved algorithm may take into account that as the aortic valve opening time reduces, the rpm should be reduced. It may be appreciated that noise may interfere with the mitral valve movements however, the noise may be filtered out such that the mitral valve movement can be accurately represented.

FIG. 15 illustrates a circuit model for the device, in which the blood pressure pump may be in parallel to the left ventricle removing blood from the left atrium. By connecting in parallel, rather than in series, the blood pumping state may be detectable from this circuit model. If the mitral valve is not opening over the cardiac cycle, this may mean that the blood pump may be pumping all the blood to the aorta or there may be suction or over pumping of the blood in the left atrium. Exclusively, small leakages in the heart valves may be determined by the detection of resistances across the diodes. Suction in the left atrium may be indicated by a low or erratic estimated pump flow rate. However, if the Mitral Valve is not opening over the cardiac cycle and there is no suction, this may mean that the blood pressure pump may be delivering all flow to the descending aorta and may be beyond the optimal set point. The controller may then reduce the blood pressure pump speed and the blood may then flow in small steps such that the mitral valve may open in the cardiac cycle while not exceeding safe the pump flow rate set with respect to the patient's posture and activity. If the mitral value is opening then the pump speed may be increased or decreased in small steps and monitoring the MVaccel amplitude value until the optimal pump speed is reached.

In another embodiment, the implantable pump may have an external controller that may operate on a basic algorithm if the external controller may not be connected. The external controller may only be programmed without the improved or smart algorithm. The external controller may house a battery or electric source such as a shower battery. The external controller may be powered by a transcutaneous energy system for short term use. The external controller may be programmable to have smart function algorithms for responding to patient physical demands or patient posture and activity states. There may be a hospital monitor to program the patient's first external and second external controllers.

In yet another embodiment, the ECG electrodes may be connected to the drive line following the heart outside the pericardium. By sensing the heart's ECG from the system's electrodes, variables are programmed to set the pump speed for the systolic and diastolic period of the heart as well as the duration of the systolic pump speed. The first accelerometer may be integrated in the pump, in which the first accelerometer may describe the XYZ position of the patient including the patient's movements and respiration. The blood pump may be implanted such that the inlet cannula protrude into the left atrium and as the heart contract, the aortic valve may open with the mitral valve already closed throughout the cardiac cycle. This motion may be imprinted on the accelerometer within the pump. The intensity of closure may determine a value called MVacc Amplitude which may be representative of the amount of acceleration produced by the mitral valve closing and the shock wave propagating through to the pump as shown in FIG. 11.

For the Basic Algorithm, atrial unloading may be done in systole when the mitral valve is closed and atrial filling happens. A baseline rpm may be set for the diastole with minimal unloading to prevent reverse flow through the blood pressure pump. In the systole, the rpm may be increased. With reference to FIG. 13, the basic algorithm may be triggered by sensing the heart's ECG from the systems electrodes and may set the pump speed for the systolic and diastolic period of the heart as well as the duration for the increased systolic pump speed. Both these speed set points and duration may be set by the clinician using the hospital monitor software, systemic BP, ECHO and clinical evaluation. Information may also be collected from ECG, accelerometers, estimated blood flow.

In another embodiment of present invention, an external controller may be adapted for driving a centrifugal implanted blood pump, wherein the pump is connected between left atrium to aorta and is driven at predetermined target speed by the controller. The external controller may detect mitral valve motion and may amend target speed to maximise target speed wherein the mitral valve motion is periodic during cardiac cycle and wherein the target speed is above a calculated minimum target speed. The external controller may detect posture and activity of user of the pump and may calculate the minimum target speed and it may classify posture and activity as one of three predetermined states which may be lying/resting, normal, or active. The external controller may also selectively fluctuate target speed between maximised target speed and minimum target speed to replicate cardiac cycle.

Although the invention has been described with reference to specific examples, it will be appreciated by those skilled in the art that the invention may be embodied in many other forms, in keeping with the broad principles and the spirit of the invention described herein.

The present invention and the described preferred embodiments specifically include at least one feature that is industrial applicable.

The invention claimed is:

1. An implantable system adapted for assisting the flow of blood from a left atrium to an aorta of an in-vivo heart, the implantable system comprising:

an inlet cannula adapted to be connected to the left atrium and an outlet cannula adapted to be connected to the aorta, wherein the inlet cannula and outlet cannula are in fluid communication with an implanted blood pressure pump;

a first accelerometer mounted on a housing of the blood pressure pump, wherein the first accelerometer is adapted for measuring mitral valve motion;

an external controller in electrical communication with at least one implanted ECG sensor adapted for detecting ECG signals, wherein the at least one implanted ECG sensor is positioned between the implanted blood pressure pump and the external controller; and wherein the external controller comprises a processor adapted to analyse detected ECG signals and the mitral valve motion; and wherein the processor dynamically adjusts a target blood pressure pump speed based on the analysed ECG signals and mitral valve motion such that blood flows from the left atrium to a left ventricle and then to the aorta.

2. The implantable system of claim 1, wherein the first accelerometer is adapted to measure a first shift of coordinate data based on movement of the first accelerometer.

3. The implantable system of claim 2, further comprising a first electrical lead in electrical communication between the implanted blood pressure pump and the ECG sensor, wherein a second accelerometer is disposed in the first electrical lead.

4. The implantable system of claim 3, wherein the second accelerometer is adapted to measure a second shift of coordinate data based on movement of the second accelerometer.

5. The implantable system of claim 4, wherein the first shift of coordinate data, and the second shift of coordinate data are analysed by the processor in order to detect patient postures and patient activities, wherein each patient activity has a predetermined blood pressure pumping speed.

6. The implantable system of claim 5, wherein the processor is adapted to calculate an optimal blood pressure pumping speed based on the patient posture and patient activity.

7. The implantable system of claim 6, wherein when the optimal blood pressure pumping speed is within the predetermined blood pressure pumping speed for a determined patient activity, the processor dynamically operates the blood pressure pump with the optimal blood pressure pumping speed.

8. The implantable system of claim 6, wherein when the optimal blood pressure pumping speed is outside of the predetermined blood pressure pumping speed for a determined patient activity, the processor dynamically operates the blood pressure pump with the predetermined blood pressure pumping speed.

9. The implantable system of claim 3, further comprising a second electrical lead, wherein a first end of the second electrical lead is connected to the ECG sensor, and a second end of the second electrical lead is connected to the external controller.

* * * * *